(12) United States Patent
Curiel et al.

(10) Patent No.: US 6,841,540 B1
(45) Date of Patent: *Jan. 11, 2005

(54) IMMUNOMODULATION BY GENETIC MODIFICATION OF DENDRITIC CELLS AND B CELLS

(75) Inventors: David T. Curiel, Birmingham, AL (US); Bryan Walter Tillman, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/591,737

(22) Filed: Jun. 12, 2000

Related U.S. Application Data

(63) Continuation-in-part of application No. 09/407,511, filed on Sep. 28, 1999, now Pat. No. 6,284,742.
(60) Provisional application No. 60/102,257, filed on Sep. 29, 1998, now abandoned.

(51) Int. Cl.[7] .................. A61K 21/70; A61K 48/00; C12N 15/74; C12N 5/06; C07H 21/02
(52) U.S. Cl. .................. 514/44; 424/93.1; 424/93.2; 424/93.21; 435/320.1; 435/325; 435/455; 536/23.1
(58) Field of Search .................. 514/44; 424/93.2, 424/93.21, 93.1; 435/320.1, 325, 455; 536/23.1; 530/350

(56) References Cited

U.S. PATENT DOCUMENTS

| | | | |
|---|---|---|---|
| 5,543,328 A | * | 8/1996 | McClelland et al. ...... 435/320.1 |
| 5,871,727 A | * | 2/1999 | Curiel ....................... 424/93.2 |
| 6,284,742 B1 | * | 9/2001 | Curiel et al. |

OTHER PUBLICATIONS

Krul et al. Induction of an antibody response in mice against human papillomavirus (HPV) type 16 after immunization with HPV recombinant salmonella strains Jun. 25, 1996 43. 44–48.*

Radoja et al. Cancer–induced defective cytotoxic T lymphocyte effector function: another mechanism how antigenic tumors escape immune–mediated killing pp. 465–479.*

Levine et al. Towards gene therapy of diabetes mellitus pp 165–171 Apr. 1999 vol. 5.*

Thomas J. Wickham et al., Journal of Virology, "Targeted Adenovirus–Mediated Gene Delivery to T Cells via CD3," Oct. 1997, vol. 71, No. 10 p. 7663–7669.*

Hidde J. Haisma et al., Cancer Gene Therapy. "Targeting of adenoviral vectors through a bispecific single–chain antibody," Jun. 2000, vol. 6, pp. 901–904.*

Robert B. Mendoza et al., Journal of Immunology, "Cutting Edge:Immunostimulatory Effects of a Plasmid Expressing CD40 Ligand (CD154) on Gene Immunization," Dec. 1997. 159:5777–5781.*

Marielle Christ et al., Immunology Letters "Gene therapy with recombinant adenovirus vectors evaluation of the host immune response", Jun. 1997 57:19–25.*

* cited by examiner

Primary Examiner—Anne M. Wehbe
Assistant Examiner—Q. Janice Li
(74) Attorney, Agent, or Firm—Frommer Lawrence & Haug; Thomas J. Kowalski

(57) ABSTRACT

The present invention provides a CD40-targeted gene delivery system and a CD40-targeted recombinant adenoviral vector for genetic manipulation of dendritic cells and B cells. Also provided are methods of using this enhanced gene delivery to immune system cells and therefore, enhancing dendritic cell-based immunotherapy.

51 Claims, 30 Drawing Sheets

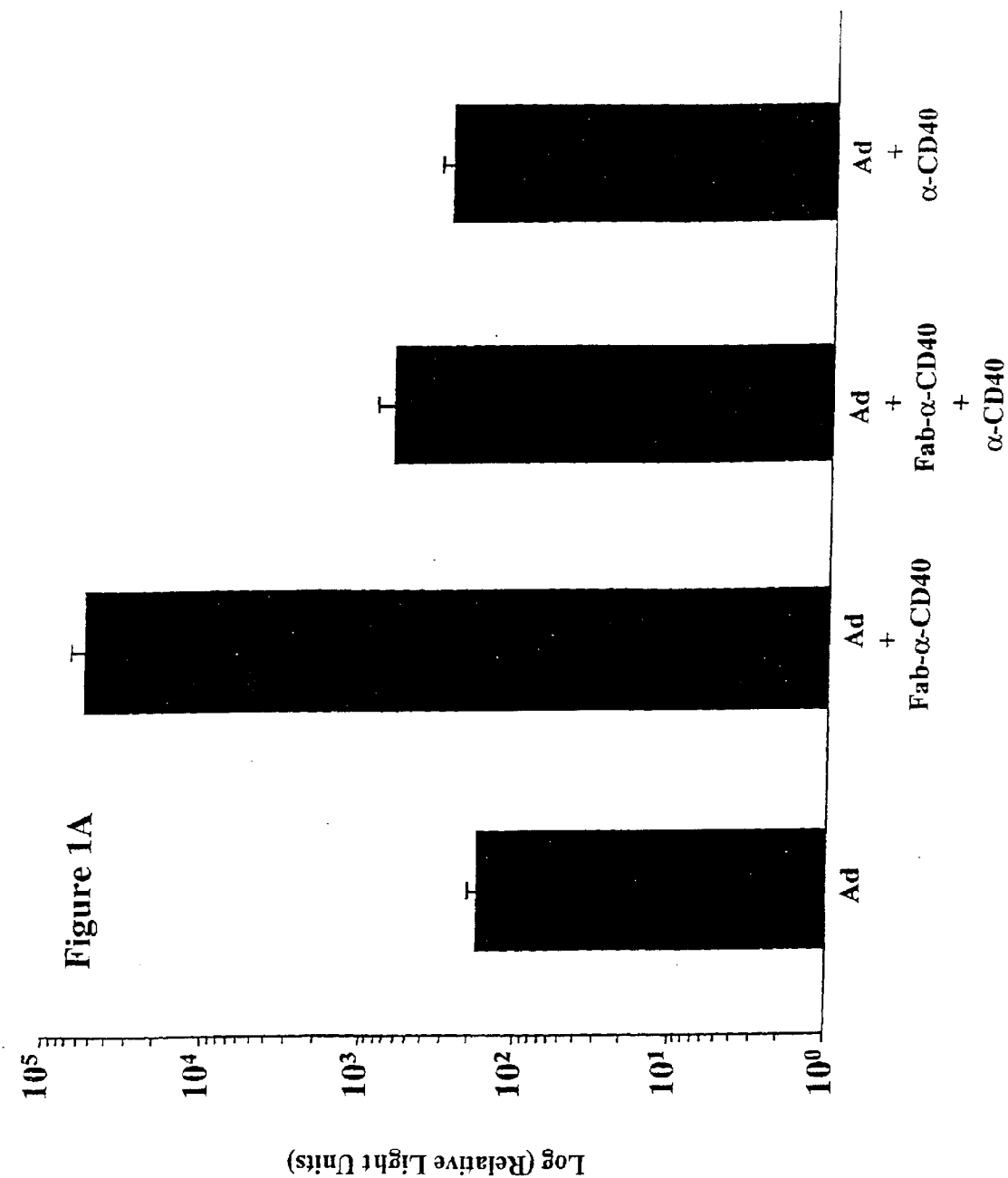

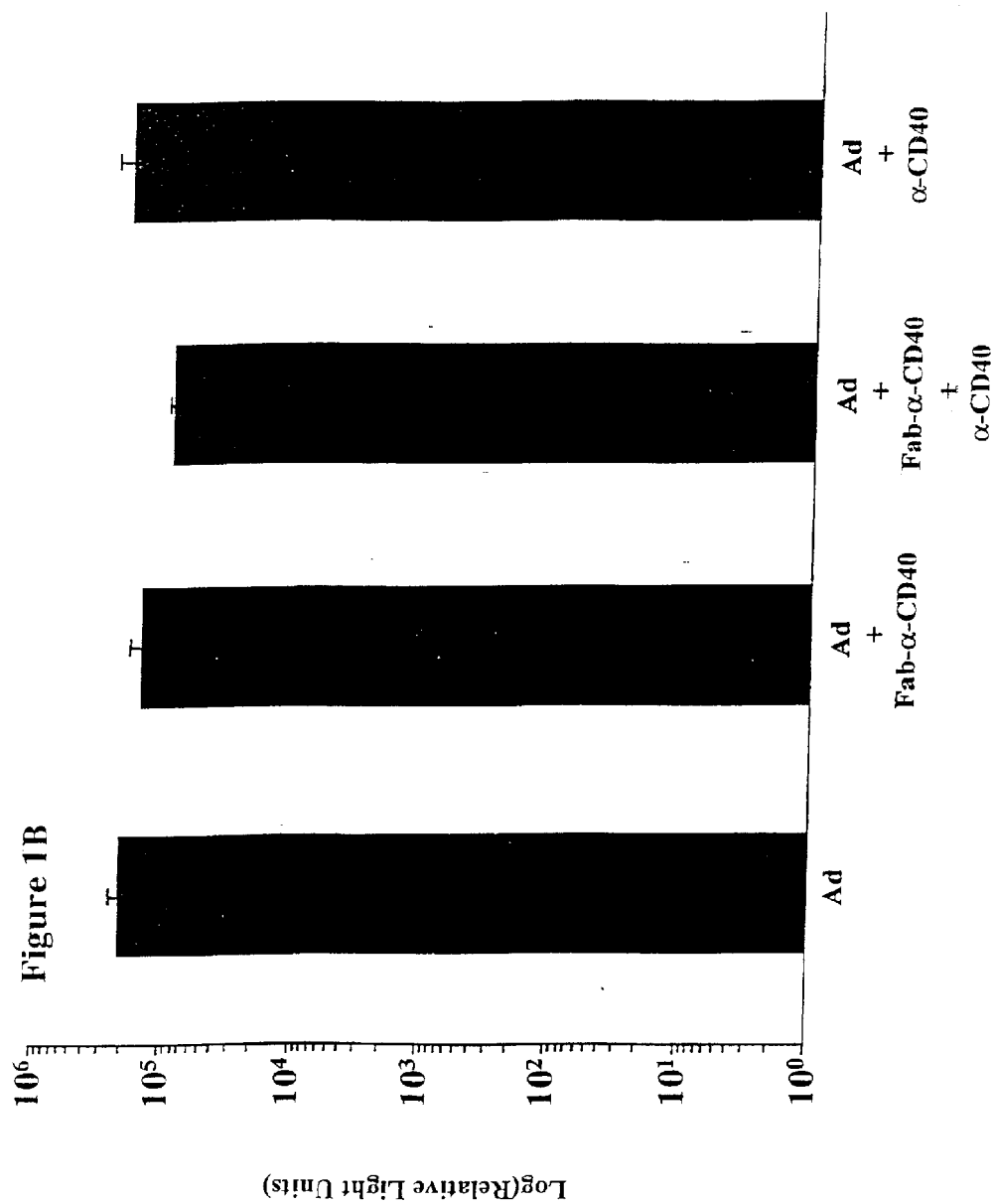

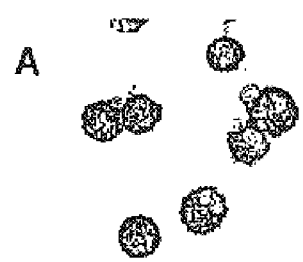
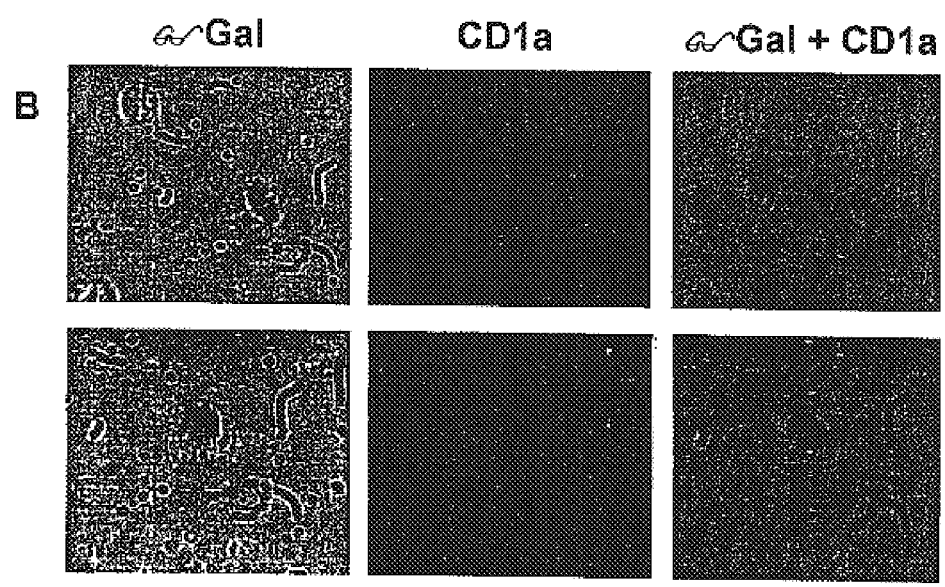
Figure 2l

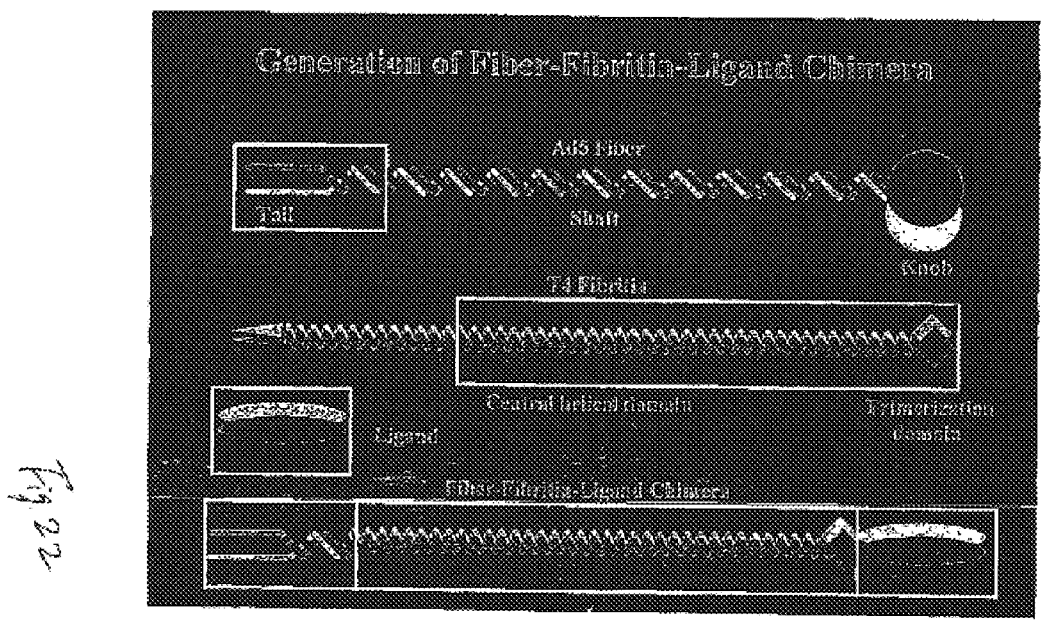

IMMUNOMODULATION BY GENETIC MODIFICATION OF DENDRITIC CELLS AND B CELLS

CROSS-REFERENCE TO RELATED APPLICATION

This application is a continuation-in-part patent application and claims the benefit of priority under 35 USC §120 of U.S. Ser. No. 09/407,511, filed Sep. 28, 1999, now U.S. Pat. No. 6,284,742, which claims benefit of priority under 35 USC §119(e) of U.S. provisional application No. 60/102,257, filed Sep. 29, 1998, now abandoned.

FEDERAL FUNDING LEGEND

This invention was produced in part using funds through grant CA74242 from the National Institutes of Health. Consequently, the federal government has certain rights in this invention.

BACKGROUND OF THE INVENTION

1. Field of the Invention

The present invention relates generally to immunology and adenoviral gene therapy. More specifically, the present invention relates to immunomodulation by genetic modification of dendritic cells and B-cells and applications of CD40-targeted adenoviral vectors in vaccination against tumor cells.

2. Description of the Related Art

An expanding body of evidence suggests that dendritic cells (DC) play a pivotal role in the immune system [Bancheareau and Steinman, 1998, Nature. 392:245]. Foremost, dendritic cells are recognized to serve as a key mediator of T cell based immunity. Stemming from their important function, dendritic cells have been proposed for utility in a number of clinical strategies, especially vaccinations. It has become clear that genetic modification of these cells can promote immunity against pathogenic entities, both infectious and tumorigenic [Reeves et al., 1996, Cancer Res. 56:5672]. Importantly, all of these strategies are predicated upon efficient vectors for gene delivery to dendritic cells. To this end, a number of approaches have been utilized, albeit generally with poor efficiency of gene transfer [Arthur et al., 1997, Cancer Gene Ther. 4:17; Van Tendeloo et al., 1998, Gene Ther. 5:700]. One candidate vector for gene delivery has been replication defective adenoviral vector. This vector has been suggested to be well suited for clinical applications by virtue of its high titer, efficiency gene delivery and exuberant gene expression.

In spite of these theoretical advantages, the relative resistance of dendritic cells to adenoviral vector infection has confounded obtaining the full benefit of gene based immunotherapy strategies. [Arthur et al., 1997, Cancer Gene Ther. 4:17; Dietz and Vuk-Pavlovic, 1998, Blood. 91:392]. The phenomenon of dendritic cell resistance to adenoviral mediated gene transfer may be based upon the paucity of adenoviral entry receptors. In permissive cells, the projecting adenoviral fiber-knob protein mediates binding to the cell surface coxsackie-adenovirus receptor (CAR) followed by interaction with and internalization of the virion by either of the αv integrins αvβ3 or αvβ5 [Bergelson et al., 1997, Science, 275:1320]. High efficiency gene transfer independent of CAR expression by means of adenovirus targeted by bispecific entities to alternate cellular receptors has been shown [Douglas et al., 1996, Nature Biotech. 14:1574].

As a result of advances in the identification of tumor specific and tumor associated antigens, antigen directed immunotherapy is emerging as a rational approach for the treatment of cancer. To this end, dendritic cells are regarded as the predominant antigen presenting cell of the immune system; the role of "mature" dendritic cells in the activation of T cells is particularly relevant to immune responses against tumors [Banchereau et al., 1998, Nature 392:245; Mayordomo et al., 1997, Stem Cells 15:94]. In many instances antigen presentation by dendritic cells is regarded as a rate limiting step in the generation of anti-tumoral immunity [Mayordomo et al., 1997, Stem Cells 15:94; Celluzzi et al., 1998, J. Immunol. 160:3081]. For these reasons, dendritic cells represent a unique junction for intervention by antigen-specific vaccination strategies.

In this regard, strategies that employ antigen pulsed dendritic cells have proven remarkably effective at protecting animal models from tumor challenge [Mayordomo et al., 1997, Stem Cells 15:94, Reeves et al., 1996, Cancer Res. 56:5672; deBruijn et al., 1998, Cancer Research 58:724; Zitvogel et al., 1996, J. Exp. Med. 183:87; Okada et al., 1998, Int. J. Cancer 78:196; Ribas et al., 1997, Cancer Research 57:2865; Tuting et al., 1997, J. Mol. Med. 75:478]. Nevertheless, the most challenging obstacle for dendritic cell based immunotherapy has been the means by which to efficiently convey antigens to dendritic cells [Arthur et al., 1997, Cancer Gene Therapy 4:17; Van Tendeloo et al., 1998, Gene Therapy 5:700].

Adenovirus (Ad) has been employed as a vector to murine dendritic cells in generation of anti-tumoral immunity [Ribas et al., 1997, Cancer Research 57:2865; Brossart et al., 1997, J. Immunol. 158:3270; Kaplan et al., 1999, J. Immunol. 163:699; Gong et al., 1997, Gene Ther. 4:102; Song et al., 1997, J. Exp. Med. 186:1247]. The inefficiency of adenovirus mediated gene transfer, however, is likely to become problematic for large scale vaccinations.

Thus, the prior art is deficient in methods for transducing dendritic cells and B-cells for immunomodulatory purposes. Further, the prior art is deficient in effective methods of enhancing efficacy of dendritic cell-based vaccination. The present invention fulfills this long-standing need and desire in the art.

SUMMARY OF THE INVENTION

A bispecific antibody was generated through chemical conjugation of antibodies with affinities for the adenovirus fiber-knob and a dendritic cell receptor, CD40. The present invention shows that CD40 targeted adenovirus mediates dramatic enhancements in gene transfer to monocyte- and bone marrow-derived dendritic cells and that these enhancements can be attributed to a quantitative increase in the number of cells transduced. Additionally, the present invention shows that this enhancement is specific to the CD40 epitope recognized by the antibody through successful blockade with the parent monoclonal antibody, and failure of the conjugate to mediate gene transfer on CD40 negative lines. Furthermore, an upregulation of several well documented dendritic cell maturational markers and enhanced allo-MLR by these cells was observed after infection with a retargeted vector. The dual role of CD40 in this scenario as both a surrogate adenovirus receptor and a powerful trigger of dendritic cell maturation may prove fortuitous as a retargeting strategy to this critical cell type of the immune system.

Additionally, the present invention demonstrates that CD40 targeted adenoviral vectors by means of bispecific antibodies can enhance gene transfer to murine dendritic cells and initiate phenotypic changes characteristic of dendritic cell maturation. To explore the in vivo potential of this strategy, this targeting approach was coupled with an adenovirus vector carrying the gene for a tumor antigen. In particular, the human papillomavirus (HPV) E7 antigen was employed which represents a target for antigen specific immunity of cervical cancer. It was found that relative to dendritic cells infected by untargeted adenovirus, dendritic cells infected by AdE7 targeted to the receptor CD40 enhanced protection against HPV-16 induced tumor cells in a murine model. Moreover, pre-immunization of animals with adenovirus infected dendritic cells prior to E7 vaccination was found to only moderately reduce vaccine efficacy. These findings suggest that use of retargeted adenoviral vectors may enhance the potency of dendritic cell-based vaccinations.

The present invention is also drawn to targeted transduction of cutaneous dendritic cell in ex vivo cultured human skin explants, demonstrating a more selective in situ transduction of $CD1\alpha^+$ cutaneous dendritic cell achieved by the targeting of Ad vectors to CD40 without interfering with their capacity to migrate.

Alternatively, the CD40-targeted adenovirus may be genetically modified, wherein the fiber proteins of the adenovirus are genetically modified. Such genetically modified Ad is further targeted to CD40 and used for enhancing the potency of dendritic cell-based vaccination.

One object of the present invention is to provide a gene delivery system and method for the genetic manipulation of immune system cells.

In one embodiment of the present invention, there is provided a gene delivery system for genetically manipulating immune system cells, comprising an adenovirus and a component recognizing CD40 antigen. Specifically, the component recognizing CD40 antigen is a bispecific conjugate comprising a first antibody, or fragment thereof, directed against a fiber-knob protein of the adenovirus and a second antibody, or fragment thereof, directed against CD40 antigen.

In another embodiment of the present invention, the gene delivery system further comprises a therapeutic gene, selected from the group consisting of a gene encoding a tumor antigen, a gene encoding an antigen for an infectious agent, a gene encoding a cytotoxic agent and a gene encoding an immunomodulatory agent.

In yet another embodiment of the present invention, there is provided a method for genetically manipulating immune system cells in an individual in need of such treatment by administering to the individual the gene delivery system disclosed herewith. Generally, such method is useful in treating an individual having a disease such as cancer, infectious disease, allotransplant rejection, xenotransplant rejection or autoimmunity disease.

Another object of the present invention is to provide an adenovirus vector capable of targeting, transducing and immunomodulating immune system cells, such as dendritic cells and B cells.

In one embodiment of the present invention, there is provided a recombinant immunomodulatory adenovirus, comprising an adenoviral vector and a bispecific antibody, wherein the bispecific antibody comprises a first antibody, or fragment thereof, recognizing a fiber-knob protein of the adenovirus and a second antibody, or fragment thereof, recognizing CD40 antigen. Specifically, the bispecific antibody may be a product of gene fusion.

In another embodiment of the present invention, the recombinant adenoviral vector may further carry a therapeutic gene, selected from the group consisting of a gene encoding a tumor antigen, a gene encoding an antigen for an infectious agent, a gene encoding a cytotoxic agent and a gene encoding an immunomodulatory agent.

In still another embodiment, there is provided a method of immunomodulation in an individual in need of such treatment by administering to the individual the recombinant immunomodulatory adenovirus disclosed herewith. Generally, such a method is useful in treating an individual having a disease such as cancer, infectious disease, allotransplant rejection, xenotransplant rejection or autoimmunity disease. Additionally, administration of the immunomodulatory adenovirus is selected from the group consisting of systemic administration, intradermal administration and ex vivo administration.

The present invention also provides a recombinant adenoviral vector and gene delivery system, comprising a genetically modified adenovirus, wherein the modification targets the vector to CD40. Specifically, the fiber of the adenovirus is replaced with two protein moieties, one initiates and maintains the trimeric configuration of the fiber protein (e.g. a bacteriophage fibritin molecule), and the other serves as a receptor-specific cell-binding ligand (e.g. CD40 ligand). Or, the fiber knob domain of the adenovirus is replaced with globular domain of CD40 ligand, wherein CD40 ligand serves both as trimerization and ligand domains. Still preferably, the gene delivery system further comprises a tumor antigen expression cassette inserted into the E1 region of the modified adenovirus.

Furthermore, the gene delivery system containing a genetically modified adenoviral vector may be used for enhancing dendritic cell-based immunotherapy in an individual in need of such treatment.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 1A–1B show that adenoviral targeted by Fab-anti-CD40 mediates enhanced magnitude of gene transfer that is specific for CD40. Monocyte derived dendritic cells (FIG. 1A) or the glioma cell line D65 (FIG. 1B) preincubated in either the presence or absence of unconjugated anti-CD40 monoclonal antibody were infected with AdCMVLuc either alone or complexed with Fab-anti-CD40. After 24-hour incubation, cells were assessed for expression of luciferase.

FIG. 21A shows the morphology of migrated cells stained for HLA-DR from skin explants 48 hours after injection with 100 ng GM-CSF (100×). FIG. 21B shows β-Gal expressing CD1α+ DC migrated from a skin explant injected with GM-CSF and Ad-LacZ complexed to the CD40-targeting conjugate (400×).

FIG. 22 shows schematic representation of the generation of Ad5 fiber-T4 fibritin chimeras containing targeting ligands. Key components of the fiber-fibritin-ligand chimera and their sources are shown. In a fiber-fibritin-ligand chimera, the tail of the fiber anchors the chimera in the Ad virion, a fragment of the fibritin provides the trimerization function, while a ligand allows for receptor-specific binding.

FIG. 23A shows analysis of protein trimerization in an SDS-PAGE. Monomeric and trimeric forms of the fiber-fibritin-linker and fiber-fibritin-linker-RGD proteins present in denatured and native samples are indicated by arrows. FIG. 23B shows binding of fiber-fibritin-linker-RGD chimera to αvβ3 integrin. Data were obtained in an ELISA assay.

DETAILED DESCRIPTION OF THE INVENTION

Figure 2:
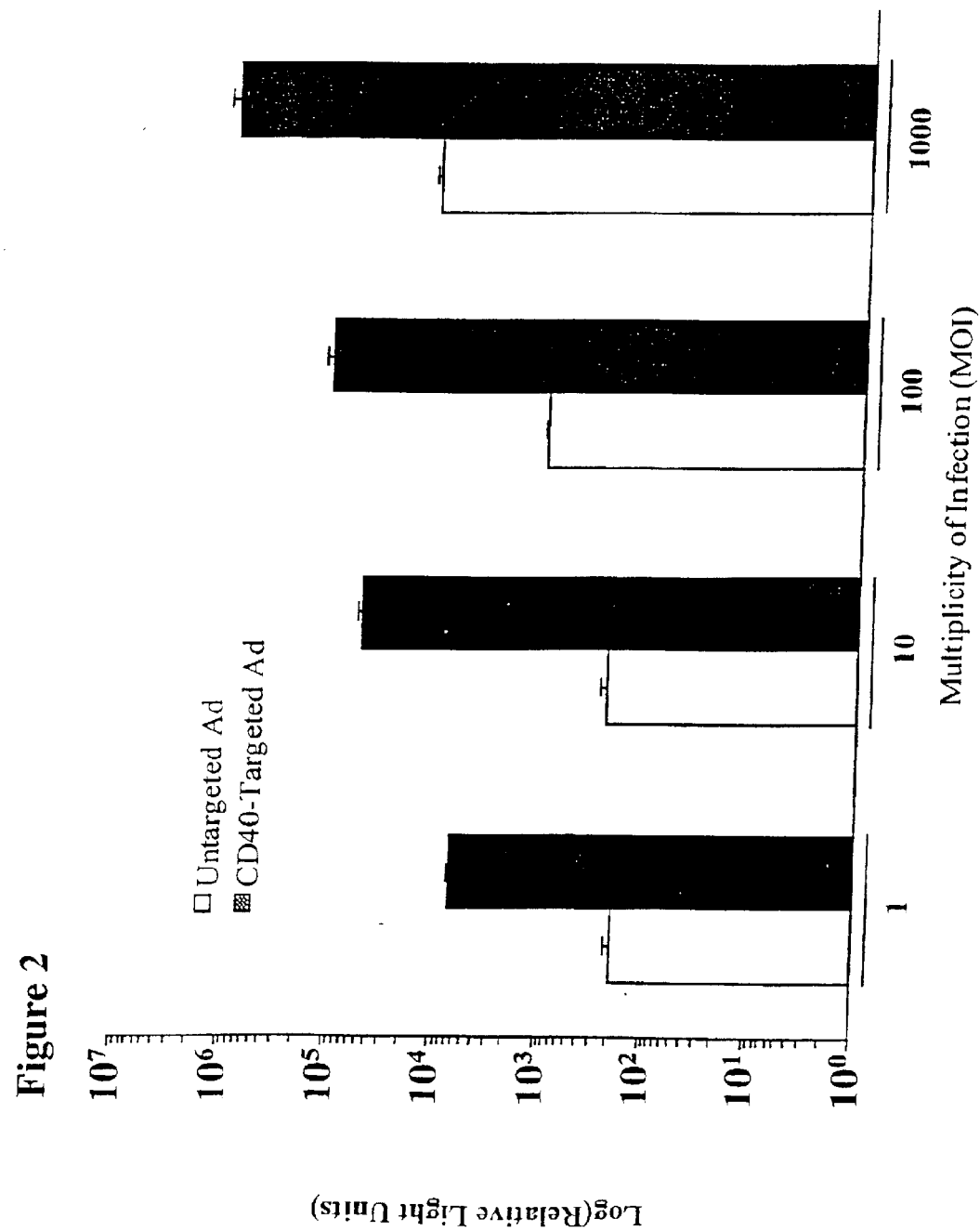
FIG. 2 shows that targeting of adenoviral to CD40 reduces the viral MOI necessary to attain a given level of gene expression. Virus, either in the presence or absence of Fab-anti-CD40 conjugate, was incubated briefly and subsequently serially diluted to correspond to Multiplicity of Infections (MOI's) of 1000, 100, 10, and 1. Monocyte derived dendritic cells were infected and cells were assayed at 24 hours for luciferase expression.

A number of studies have highlighted the important consequences of genetically modified dendritic cells. A vector to achieve efficient gene transfer to this cell type becomes paramount to many immunomodulatory strategies and yet current vector systems have struggled with low efficiency gene transfer. Adenovirus has been used in the context of dendritic cell transduction, but its efficiency of gene delivery has proven suboptimal. By means of bispecific antibodies, the present invention successfully demonstrates enhanced gene transfer to monocyte- and bone marrow-derived dendritic cells by retargeting the adenovirus to CD40, a marker widely expressed on dendritic cells. CD40-targeted virus demonstrated both dramatic and quantitative improvements in gene transfer compared to untargeted virus. This gene transfer has been demonstrated to be specific for CD40 as illustrated by both successful blocking with the parental monoclonal antibody as well as by the absence of gene transfer in CD40 negative cells. These features would be anticipated to reduce the dose of virus required for a given level of transduction and would, therefore, be expected to decrease vector-related toxicity and curtail ectopic gene delivery.

One aspect of the novelty of this present system is the capacity of the vector itself to modulate the immunological status of the monocyte derived dendritic cells. This vector induces dendritic cell maturation as demonstrated phenotypically by increased expression of CD83, MHC, and costimulatory molecules as well as functionally by an enhanced allostimulatory capacity in a Mixed Lymphocyte Reaction (MLR). In comparing this vector to other adenoviral based gene transfer vectors, it has become apparent that the profound effects observed on dendritic cells are specific to CD40. This approach may serve not only as a high efficiency gene transfer vector, but may also obviate the need for supplemental steps to promote dendritic cell maturation subsequent to gene delivery.

Furthermore, the present invention describes the use of a CD40-targeted adenoviral vector carrying the gene of the human papillomavirus type 16 E7 antigen for genetic modification of murine dendritic cells. Importantly, the E7 gene contains a deletion which renders the oncogenic retinoblastoma binding domain nonfunctional [Morozov et al., 1997, J. Virol. 71:3451]. Evidence was provided that dendritic cells genetically modified by targeted adenovirus can efficiently initiate antigen specific immunity towards tumors expressing HPV-16 E7. It was also demonstrated that targeting of the adenoviral vector to CD40 imparts an advantage in a vaccination context over untargeted adenoviral vectors. Such vaccinations retain their potency despite pre-immunization of animals with adenovirus infected dendritic cells.

The present invention also describes targeted transduction of cutaneous dendritic cell in ex vivo cultured human skin explants, demonstrating a more selective in situ transduction of CD1+ cutaneous dendritic cell achieved by the targeting of adenoviral vectors to CD40 without interfering with their capacity to migrate.

The present invention is directed towards adenoviral vectors targeted for the CD40 cell surface antigen of dendritic cells and B cells and methods of dendritic cell and B cell transduction and maturation using a targeted adenoviral vector. The present invention is also directed towards a gene delivery system and method for immunomodulation of immune system cells by employing bispecific conjugate targeting CD40. The present invention is further directed towards a method of enhancing dendritic cell-based immunotherapy by employing the adenoviral vectors or gene delivery system disclosed herewith.

Furthermore, the present invention is directed to a genetically modified adenoviral vector targeted to CD40 and a gene delivery system containing such CD40-targeted adenoviral vector, and method of enhancing dendritic cell-based immunotherapy by employing such vector and system. Specifically, to generate genetically modified adenoviral vector, adenovirus fiber proteins are genetically modified to result in altered adenovirus tropism and differential biodistribution in vivo.

In accordance with the present invention, there may be employed conventional molecular biology, microbiology, and recombinant DNA techniques within the skill of the art. Such techniques are explained fully in the literature. See, e.g., Sambrook, Fritsch & Maniatis, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo; i.e., capable of replication under its own control. An "origin of replication" refers to those DNA sequences that participate in DNA synthesis. An "expression control sequence" is a DNA sequence that controls and regulates the transcription and translation of another DNA sequence. A coding sequence is "operably linked" and "under the control" of transcriptional and translational control sequences in a cell when RNA polymerase transcribes the coding sequence into mRNA, which is then translated into the protein encoded by the coding sequence.

In general, expression vectors containing promoter sequences which facilitate the efficient transcription and translation of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

"Recombinant DNA technology" refers to techniques for uniting two heterologous DNA molecules, usually as a result of in vitro ligation of DNAs from different organisms. Recombinant DNA molecules are commonly produced by experiments in genetic engineering. Synonymous terms include "gene splicing", "molecular cloning" and "genetic engineering". The product of these manipulations results in a "recombinant" or "recombinant molecule".

A cell has been "transformed", "transfected" or "transduced" with exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a vector or plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations. An organism, such as a plant or animal, that has been transformed with exogenous DNA is termed "transgenic".

The term antibody herein is intended to encompass both polyclonal and monoclonal antibodies. The term antibody is also intended to encompass whole antibodies, biologically functional fragments thereof, chimeric and humanized antibodies comprising portions from more than one species. Also encompassed in the term antibody are antibodies and biologically functional fragments thereof with alterations in glycosylation or with alterations in complement binding function.

Biologically functional antibody fragments are those fragments sufficient for binding of the antibody fragment to CD40 to occur, such as Fab, Fv, F(ab')$_2$, and sFv (single-chain antigen-binding protein) fragments. Antibody fragments can be generated by methods known to those skilled in the art, e.g. by enzymatic digestion of naturally occurring or recombinant antibodies, by recombinant DNA techniques using an expression vector that encodes a defined fragment of an antibody, by chemical synthesis, or by using bacteriophage to display and select polypeptide chains expressed from a V-gene library. One can choose among these or whole antibodies for the properties appropriate to a particular method.

As used herein, the term "immunomodulatory" shall refer to the capacity to promote or suppress immunity towards cancer, infectious agents, autoimmune antigens, or allo/xeno transplants.

As used herein, the term "maturation", as it refers to immune system cells, refers to expression of specific surface markers, production of defined soluble factors, or enhanced performance in a Mixed Lymphocyte Reaction all of which are known to be characteristic of a cell which has become more efficient in the capacity to elicit a response from effector cells, such as T cells.

As used herein, the term "CD40 antigen" shall refer to a member of the TNF receptor (TNFR) family. It serves as the receptor for CD40 Ligand (gp39). This molecule is known to be expressed on B-lymphocytes, monocytes, dendritic cells, endothelium, epithelial cells, and fibroblasts. Of note, this molecule is known to be especially prevalent in areas of activated endothelium (such as chronic inflammation) and on the vessels of Kaposi's sarcoma.

It is specifically contemplated that pharmaceutical compositions may be prepared using the novel adenoviral vector of the present invention. In such a case, the pharmaceutical composition comprises the novel adenoviral vector of the present invention and a pharmaceutically acceptable carrier. A person having ordinary skill in this art would readily be able to determine, without undue experimentation, the appropriate dosages and routes of administration of this adenoviral vector of the present invention. When used in vivo for therapy, the adenoviral vector of the present invention is administered to the patient or an animal in therapeutically effective amounts, i.e., amounts that eliminate or reduce the tumor burden due to an immunomodulatory effect. It will normally be administered parenterally, preferably intravenously, but other routes of administration will be used as appropriate. The dose and dosage regimen will depend upon the nature of the disease and its population, the characteristics of the particular vector, e.g., its therapeutic index, the patient, the patient's history and other factors. The amount of adenoviral vector of the present invention administered will typically be in the range of about 0.001 to about 500 mg/kg of patient weight. The schedule will be continued to optimize effectiveness while balanced against negative effects of treatment. See Remington's Pharmaceutical Science, 17th Ed. (1990) Mark Publishing Co., Easton, Pa.; and *Goodman and Gilman's: The Pharmacological Basis of Therapeutics* 8th Ed (1990) Pergamon Press.

For parenteral administration, the adenoviral vector will most typically be formulated in a unit dosage injectable form (solution, suspension, emulsion) in association with a pharmaceutically acceptable parenteral vehicle. Such vehicles are preferably non-toxic and non-therapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives. The adenoviral vector will typically be formulated in such vehicles at concentrations of about 0.001 mg/ml to 500 mg/ml.

Thus, the present invention is directed to a gene delivery system for the genetic manipulation of immune system cells, comprising: (a) an adenovirus; and (b) a component recognizing CD40 antigen. Preferably, the component recognizing the CD40 antigen comprises a first antibody, or fragment thereof, directed against a fiber-knob protein of the adenovirus, and a second antibody, or fragment thereof, directed against CD40 antigen. Representative examples of antibody directed against CD40 antigen are G28.5 and FGK45.

In one aspect, the first antibody and second antibody may be genetically fused together. This gene delivery system can be used to transduce, immunomodulate or maturate immune system cells. Furthermore, this system may also comprise a therapeutic gene. Representative therapeutic genes include a gene encoding a tumor antigen, a gene encoding an antigen for an infectious agent, a gene encoding an autoimmune antigen, an immunomodulatory gene and a gene encoding a cytotoxic agent. A more specific example of tumor antigen is human papillomavirus type 16 E7 antigen. Representative immune system cells which can be transduced and immunomodulated using this system include of dendritic cells and B-cells. More specifically, the dendritic cells are monocyte-derived dendritic cells, bone marrow-derived dendritic cells, and cutaneous dendritic cells.

The present invention is also directed to a method for genetically manipulating immune system cells in an individual in need of such treatment, comprising the step of administering the gene delivery system disclosed herewith to the individual. This method may be useful wherein the individual has a disease selected from the group consisting of cancer, an infectious disease, allotransplant rejection, xenotransplant rejection and an autoimmune disease. Preferably, administration of the gene delivery system is selected from the group consisting of systemic administration, intradermal administration and ex vivo administration.

The present invention is yet further directed to a method for enhancing dendritic cell-based immunotherapy by employing the gene delivery system disclosed herewith. An example of immunotherapy is vaccination. Preferably, administration of the gene delivery system is selected from the group consisting of systemic administration, intradermal administration and ex vivo administration.

The present invention also provides a recombinant adenoviral vector for the genetic manipulation of immune system cells, comprising a first antibody, or fragment thereof, directed against a fiber-knob protein of the adenovirus and a second antibody, or fragment thereof, directed against CD40 antigen. A preferred antibody directed against CD40 antigen is G28.5 or FGK45. This recombinant adenoviral vector can be used to transduce, immunomodulate and/or maturate immune system cells.

In one aspect, the recombinant adenoviral vector may further comprise a therapeutic gene such as a gene encoding a tumor antigen, a gene encoding an antigen for an infectious agent, a gene encoding an autoimmune antigen, an immunomodulatory gene or a gene encoding a cytotoxic agent.

The present invention further provides a method for genetically manipulating immune system cells in an individual in need of such treatment by administering the recombinant adenoviral vector disclosed herewith to the individual. Such individuals may have a disease such as cancer, an infectious disease, allotransplant rejection, xenotransplant rejection or an autoimmune disease. Preferably, administration of the recombinant adenoviral vector is selected from the group consisting of systemic administration, intradermal administration and ex vivo administration.

Still further provided in the present invention is a method for enhancing dendritic cell-based immunotherapy by employing the recombinant adenoviral vector disclosed herewith. An example of immunotherapy is vaccination. Preferably, administration of the recombinant adenoviral vector is selected from the group consisting of systemic administration, intradermal administration and ex vivo administration.

The present invention additionally provides a recombinant adenoviral vector and gene delivery system, comprising a genetically modified adenovirus, wherein the modification targets the vector to CD40. Specifically, the fiber of the adenovirus is replaced with two protein moieties, one initiates and maintains the trimeric configuration of the fiber protein (e.g. a bacteriophage fibritin molecule), and the other serves as a receptor-specific cell-binding ligand (e.g. CD40 ligand). Or, the fiber knob domain of the adenovirus is replaced with globular domain of CD40 ligand, wherein CD40 ligand serves both as trimerization and ligand domains. Still preferably, the gene delivery system further comprises a tumor antigen expression cassette inserted into the E1 region of the modified adenovirus. A representative example of tumor antigen is human papillomavirus type 16 E7 antigen. Furthermore, the gene delivery system containing a genetically modified adenoviral vector may be used for enhancing dendritic cell-based immunotherapy in an individual in need of such treatment.

The following examples are given for the purpose of illustrating various embodiments of the invention and are not meant to limit the present invention in any fashion:

EXAMPLE 1

CD40-Targeted Adenovirus Induces Dendritic Cell Maturation

Culture of monocyte-derived dendritic cells (MoDC) Peripheral Blood Mononuclear Cells (PBMC) were isolated from heparinized peripheral blood by density centrifugation over Lymphoprep (Nycomed AS, Oslo, Norway) and cryopreserved in RPMI 1640 medium supplemented with 12.5% DMSO and 25% FCS, which has previously been described as the optimal cryopreservative medium for monocyte derived dendritic cells and their precursors (Makino and Baba). Fresh or cryopreserved peripheral blood mononuclear cells were suspended at a concentration of 3 to 5 million cells per ml in Iscove's modified Dulbecco's medium containing 50 U/mL penicillin-streptomycin, 1.6 mM L-Glutamine, 0.01 mM β-mercaptoethanol (complete medium), and 10% FCS and were allowed to adhere to the bottom of plastic culture flasks (NUNC, Intermed, Denmark). After 2 hours at 37° C., non-adherent cells were removed by rinsing with PBS. The adherent cells were cultured for a further 6 days in complete medium with 10% FCS supplemented with 1000 U/ml rIL-4 (CLB, Amsterdam, The Netherlands) and 100 ng/mL GM-CSF. Loosely adherent cells with typical dendritic cell morphology were harvested (adherent cells were detached by incubation with 0.5 mM EDTA in PBS) and used for FACS analysis or adenovirus mediated gene transfer.

Mixed Lymphocyte Reaction

For allogeneic and autologous Mixed Lymphocyte Reaction, monocyte derived dendritic cells were added as stimulator cells to roundbottom 96-well culture plates (Nunclon Delta, Intermed, Denmark) at graded doses. Nonadherent lymphocyte fractions were used as a source for responder cells. Per well $1 \times 10^5$ lymphocytes were added to the allogeneic or autologous monocyte derived dendritic cells at the indicated Responder/Stimulator ratios (R:S). The cells were cultured for 3 days in complete medium with 10% Human Pooled Serum (CLB, Amsterdam, The Netherlands). During the last 18 hours, [$^3$H]-thymidine was added (0.4 mCi per well) (Amersham, Aylesbury, UK), after which the cells were harvested onto fiberglass filters and [$^3$H]-thymidine incorporation was determined using a flatbed liquid scintillation counter (Wallac, Turku, Finland).

Phenotypic Analyses

Cell staining was performed using monoclonal antibodies (MoAbs) directly conjugated to Fluorescein Isothiocyanate (FITC) or to Phycoerthrin (PE). The antibodies used were HB15 (CD83), BL6 (CD1a), BU15 (CD11c), MAB89 (CD40), (Immunotech, Marseille, France), SK7 (CD3), 4G7 (CD19), B73.1 (CD16), MoP9 (CD14), NCAM 16.2 (CD56), L243 (HLA-DR), 2A3 (CD25) (Becton Dickinson, San Jose, Calif.), 2331 (CD86), G46-2.6 (HLA A, B, C), HA58 (CD54), and TU169 (HLA-DQ) (Pharmingen, San Diego, Calif.). The samples were analyzed on a FACStar using Cellquest FACS analysis software (Becton Dickinson).

When cells were infected with adenoviral prior to analysis, all values for conjugate or virus used in microscale luciferase assays were proportionately increased for the larger number of cells to be infected. Cells were infected in batches of 1 million cells using AdCMVLuc. Cells were infected in a similar manner to that used for luciferase gene transfer analysis, with the only exception that cells were left in microcentrifuge tubes for the entire 24 hour incubation after washing and addition of complete medium. At 24 hours, the cells were assessed by flow cytometry for expression of maturation associated surface markers.

Viruses and Cell Lines

AdCMVLuc, a first generation E1-, E3-deleted vector expressing firefly luciferase from the CMV immediate early promoter, was obtained from Robert Gerard (University of Leuven, Leuven, Belgium). Viruses were propagated and plaque titered on the permissive line 293 and purified by double centrifugation on CsCl gradients. All virus aliquots were stored at—80° C. until use. Murine monoclonal antibody RmcB to human coxsackie/adenovirus receptor (from Dr. Robert Finberg, Dana Farber Cancer Institute) has been described previously. Murine monoclonal antibody LM609 to $\alpha v \beta 3$ and P1F6 to $\alpha v \beta 5$ integrin were purchased from Chemicon (Temecula, Calif.) and Gibco BRL (Gaithersburg, Md.) respectively. The neutralizing murine monoclonal antibody 1D6.14 specific for the carboxy-terminal, receptor binding domain of adenoviral serotype 5 has been described. The hybridomas G28.5, producing anti-CD40 monoclonal antibodies (ATCC#:9110-HB) and TS2/16.2.1 (ATCC#: 243-HB; "TS2") producing monoclonal antibodies against the $\beta 1$ integrin, were purchased from ATCC. Both hybridomas were used to generate ascites in SCID mice.

Antibodies were purified on an FPLC chromatography system using HiTrap Protein A column (Pharmacia) and the MAPS binding buffer system (Bio-Rad). The 1D6.14 monoclonal was digested to a Fab fragment using immobilized papain (Pierce) and fragments were purified by negative selection of Fc fragments using HiTrap Protein A columns.

Antibodies and Conjugates

Both 1D6.14-Fab and monoclonal antibodies G28.5 and TS2 were concentrated to 10 mg/mL in Borate Buffer. Chemical conjugation of the Fab to mAb in a 1:1 molar ratio was performed as described [Segal, D. and B. Bast, 1994, Production of bispecific antibodies. Editors: Coligan, et al., Current Protocols in Immunology. John Wiley and Sons, New York, Vol. 1. Sec. 2.13.1–2.13.16]. Conjugate was purified on a HR 10/30 Superose 12 column using FPLC (Pharmacia, Piscataway, N.J.) in Borate buffer pH 8.5, wherein the fractions were pooled that corresponding to a 1:1 ratio of anti-receptor antibody to Fab, at an approximate molecular weight of 200 kDa.

Protocol for Ad infection and Luciferase Analysis

Nonadherent monocyte derived dendritic cells were collected and mixed with the 0.5 mM EDTA released adherent cell fraction followed by washing in complete RPMI containing 2.5% FCS. Twenty-four thousand cells in a volume of 50 µl were distributed to individual microcentrifuge tubes in triplicate for each test condition. The use of microcentrifuge tubes enabled simplified infection and washing of cells, which represented both adherent and nonadherent fractions. Conjugate and virus were incubated for 30 minutes at room temperature in a minimal volume of under 10 μl per each test condition's worth of virus. Following incubation the mixture was diluted such that 100 μL was used to infect each microcentrifuge tube of cells. The amount of virus in this volume corresponded to a multiplicity of infection of 100. Microcentrifuge tubes containing the infection mixture were placed at 37° C. for 1 hour. Subsequently, to remove unbound virus, cells were washed in the tubes with PBS, centrifuged, and the supernatant aspirated. Pelleted cells were resuspended in 1 mL of RPMI 10% FCS and moved to individual wells of a polylysine coated 24-well plate for overnight incubation. Use of polylysine coated wells enabled simpler processing in subsequent luciferase assays by anchoring of both adherent and suspension fractions to the well surface. Following 24 hours of incubation post infection, supernatant was aspirated from all wells and the cells were processed using the Promega Luciferase Assay Kit. Briefly, cells were lysed directly on the plate and subjected to one freeze thaw cycle. The lysates were analyzed by mixture with luciferase substrate and immediate evaluation on a Lumat luminometer.

For blocking experiments, cells were blocked with the parental (unconjugated) G28.5 monoclonal prior to infection. Due to the rapid internalization kinetics previously reported for this monoclonal, all blocking was performed at 4° C. to minimize receptor modulation from the cell surface. After 30 min of incubating cells with the blocking agent, virus complexed with the optimal amount of Fab-G28.5 was added directly to the cells and incubated further for a period of 30 min before washing and transition to the 24-well plate at 37° C. For blocking with Fab, virus was preincubated with an excess of a previously determined neutralizing concentration of 1D6.14 Fab. In this regard, Fab was merely substituted in place of conjugate for the indicated conditions.

Conjugate Titration to Ascertain the Optimal Amount of Conjugate for Retargeting To determine the amount of retargeting conjugate necessary to optimally coat an adenovirus, the conjugate was titrated on a predetermined number of viral particles at an MOI of 100, wherein gene transfer was measured in terms of luciferase expression as relative light units, RLU, in monocyte derived dendritic cells. Monocyte derived dendritic cells were infected with AdCMVLuc preincubated with increasing concentrations of Fab-G28.5. Further increases in the conjugate: virus ratio proved to reduce the magnitude of retargeted gene transfer, presumably stemming from competition for CD40 binding by excess Fab-G28.5 conjugate. This titration tested given masses of conjugate ranging from 0.01 ng to 2000 ng/well with intervals at every half $\log^{10}$ of mass following incubation with $2.4 \times 10^6$ virions. The mass of conjugate corresponding to the highest levels of luciferase gene expression was termed an "optimal dose" and was used in all subsequent experiments.

GFP Reporter Gene to Demonstrate Quantitative Gene Transfer

To ensure that the gene transfer observed with luciferase correlated to an actual increased number of cells transduced, cells were also infected with adenoviral carrying the gene for GFP. As for cells undergoing flow cytometry based marker analysis, monocyte derived dendritic cells were batch infected using AdGFP complexed to the optimal ratio of Fab-G28.5 conjugate. Twenty-four hours post-infection, positive cells were visualized using flow cytometry.

Analysis of Differential MOI between CD40-Targeted and Untargeted Ad

Cells were batch infected with different MOI's of CD40-targeted and untargeted virus. Fab-G28.5 was complexed with AdCMVLuc at a concentration corresponding to 1000 MOI. Subsequently, this mixture was serially diluted to MOI's of 500, 100, 50, 10, and 1. Simultaneously, samples of the same MOI's of adenovirus without retargeting conjugate were prepared for comparison with targeted samples. Monocyte derived dendritic cells were then infected and analyzed for luciferase as was done in the luciferase gene transfer experiments.

Validation of Monocyte Derived Dendritic Cells

Monocyte derived dendritic cells were generated by treatment of monocytes isolated from peripheral blood with IL-4 and GM-CSF. The identity of these cells was validated in two ways. Purity was demonstrated through flow cytometry for lack of expression of CD14, CD3 and CD19. Further, the cells exhibited a dendritic cell phenotype with some veiled cells and a mixture of adherent and nonadherent fractions associated in multicellular clusters. These monocyte derived dendritic cells were negative for expression of dendritic cells maturational markers, such as CD83, and were thus immature.

Results

Observed Enhancement in Gene Transfer is Specific to CD40

To determine the amount of retargeting conjugate necessary to optimally coat an adenovirus, the conjugate was titrated on a predetermined number of viral particles at an MOI of 100, wherein gene transfer was measured in terms of luciferase expression in monocyte derived dendritic cells. Monocyte derived dendritic cells were infected with AdCMVLuc preincubated with increasing concentrations of Fab-G28.5. CD40-targeted gene transfer reached a maximum with a Fab-G28.5 conjugate-virus ratio of 30ng Fab-G28.5 per $2.4 \times 10^6$ pfu ($1.75 \times 10^8$ particles/mL as determined by $OD_{260}$). Further increases in the conjugate to virus ratio proved to reduce the magnitude of retargeted gene transfer, presumably stemming from competition for CD40 binding by excess Fab-G28.5 conjugate. At the optimal ratio of conjugate to virus, CD40 targeted adenoviral demonstrated a two $\log^{10}$ enhancement in gene transfer to monocyte derived dendritic cells, as determined by expression of the Luciferase reporter gene. This optimal dose was analyzed in several ways for its specificity to CD40.

So as to implicate the anti-CD40 antibody of the conjugate as the basis for the observed enhancements in gene transfer, cells were preincubated with the parental anti-CD40 antibody, G28.5 (FIG. 1). When cells were blocked in this manner, an expected 95% reduction in retargeted gene transfer was observed. To exclude the possibility that G28.5 mAb itself was mediating enhanced adenovirus gene transfer independent of its association with the virion, cells were preincubated with unconjugated G28.5 mAb prior to infection with untargeted adenovirus. Pretreament of cells with the G28.5 monoclonal resulting in negligible enhancements in gene transfer.

To rule out the possibility that bispecific conjugate mediated nonspecific cell binding (or more specifically, by interaction of bispecific antibody with Fc receptors on dendritic cells), an irrelevant conjugate with affinity for a marker (EGFR) absent from the surface of dendritic cells was tested. The irrelevant conjugate failed to mediate enhancements in gene transfer, further demonstrating the specificity of the observed CD40-retargeting. As a stringent test of the vector specificity, the above conditions were also tested on the CD40 negative glioma cell line, D65. The failure of adenoviral targeted by Fab-G28.5 to enhance gene expression on D65 further indicates the specificity of this vector for CD40.

Fab-G28.5 Enhances Adenovirus Mediated Gene Transfer in Different Donors and Such Retargeting Can Reduce the Viral Dose Required to Achieve a Given Level of Transgene Expression To compare the efficacy of this retargeting strategy in different donors simultaneously, CD40-targeted adenovirus was compared to untargeted adenovirus at several MOI's on monocyte derived dendritic cells (FIG. 2). These results also indicate that at a given MOI, retargeted adenovirus yields a magnitude of gene transfer seen only in untargeted adenovirus at 100-fold higher MOI. These results highlight a significant advantage of retargeted adenovirus in that for a given level of gene transfer, significantly less infectious virions per cell are required when using a CD40 retargeted adenovirus. Since larger viral doses are associated with greater direct viral mediated cytotoxicity as well as more vigorous anti-adenovirus immune response, the potential to reduce the viral dose administered has important implications for reducing toxicities associated with use of adenovirus vectors.

Figure 3:
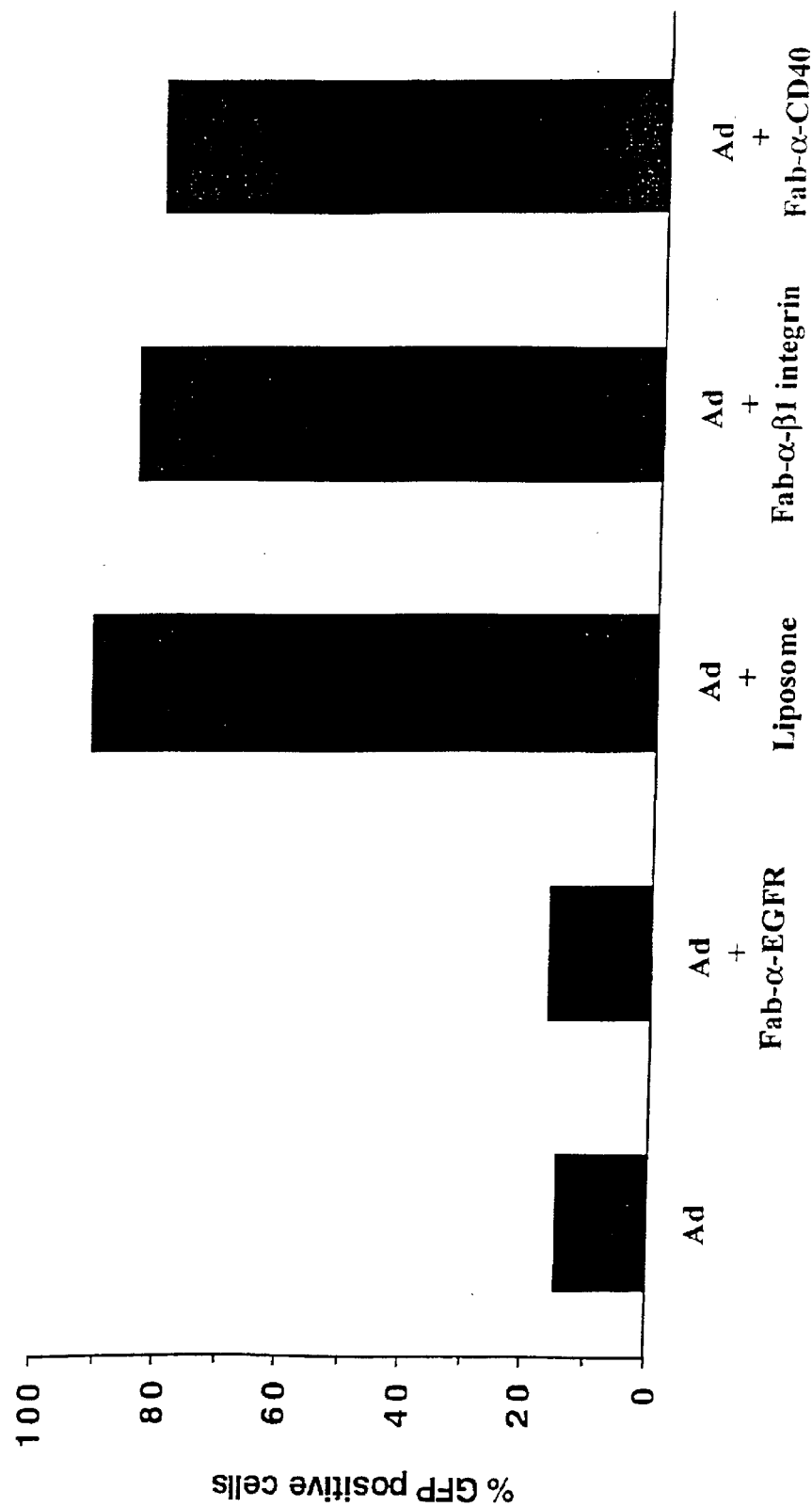
FIG. 3 shows CD40 targeted, β1 integrin targeted and liposome complexed adenoviral mediate comparable gene transfer to monocyte derived dendritic cells. Monocyte derived dendritic cells were infected with adenoviral encoding Green Fluorescent Protein (GFP) preincubated with one of the following: PBS, Fab-anti-CD40, Fab-anti-β1 integrin conjugate, Fab-anti-EGFR conjugate or Liposomes. After 24 hour incubation at 37° C., the conditions were assessed using flow cytometry for expression of GFP and are displayed as percent GFP positive cells based on analysis of 10,000 cells.

Enhancements in Gene Transfer Are Due to Quantitatively Increased Numbers of Cells Transduced While luciferase gene transfer had illustrated an overall increase in gene expression due to CD40-targeted adenovirus, the nature of this assay could not indicate whether an increased number of cells had actually been transduced. To rule out the possibility that a few transduced cells were merely exhibiting more exuberant gene expression as a result of retargeting, adenovirus containing a quantitative marker, Green Fluorescent Protein, GFP, was used. The number of cells transduced was monitored through use of flow cytometry. It was determined that compared to cells infected with untargeted adenovirus, CD40-targeted adenovirus quantitatively transduced more cells. Comparable levels of gene transfer were observed with two other methods, β1 integrin targeted adenovirus and liposome complexed adenovirus. Once again, this enhanced gene transfer was absent when an irrelevant conjugate to EGFR was used (FIG. 3).

Figure 4:
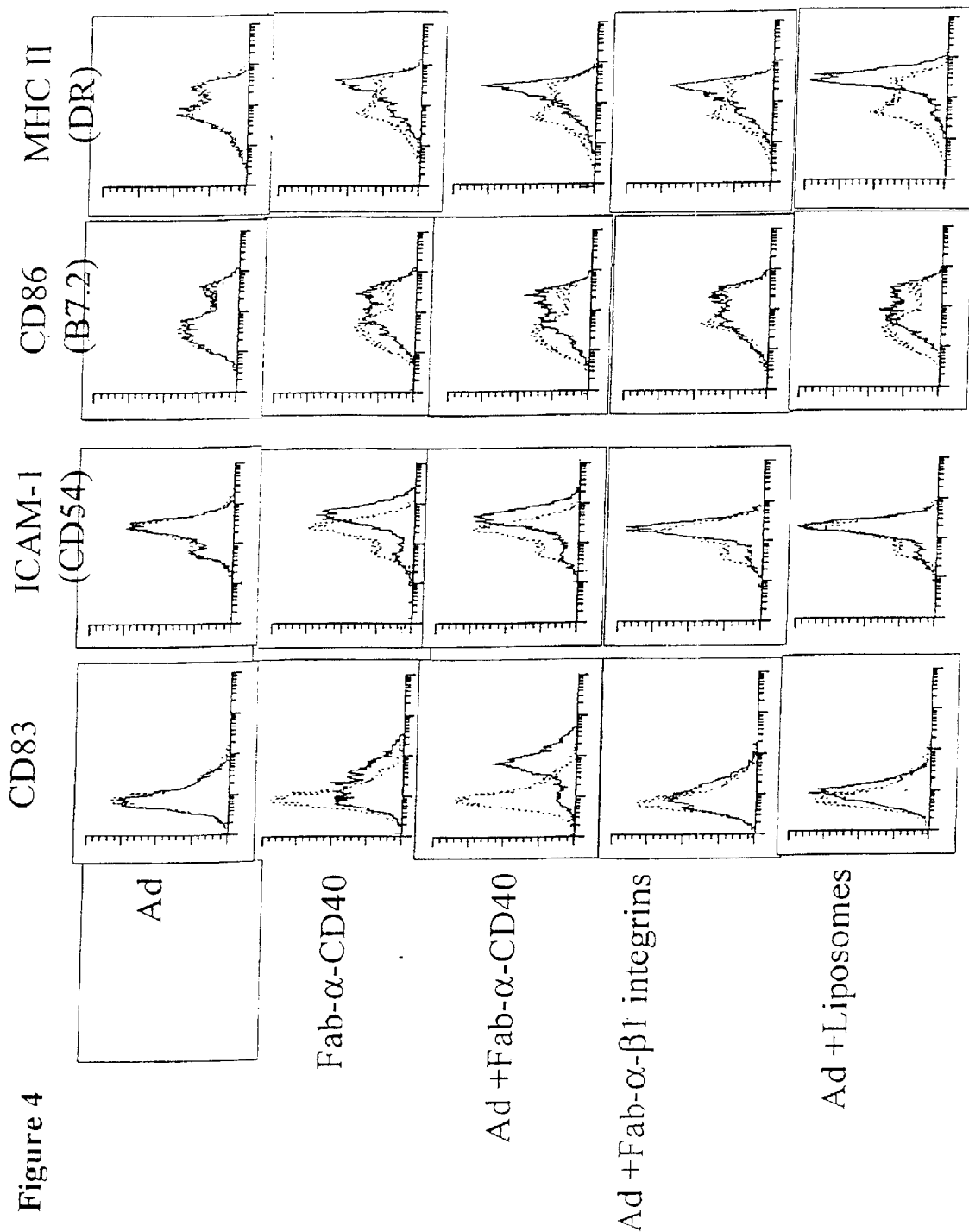
FIG. 4 shows that CD40-targeting mediates expression of dendritic cells maturational markers. Cells were treated with the indicated conditions or virus/conjugates or conjugates alone and incubated for 24 hours. Samples shown indicate expression of CD83, HLA-DR, HLA-DQ, CD86, and CD54 by flow cytometry.

MoDC Transduced by CD40-Targeted Ad Exhibit Phenotypic and Functional Characteristics of Mature Dendritic Cells Having demonstrated enhanced gene transfer efficacy, the effect of virus on dendritic cells as relates to their phenotypic and functional capacity was examined. To determine the effects of retargeted-adenoviral vectors or the retargeting conjugates alone on dendritic cell maturation, several markers were analyzed using flow cytometry (FIG. 4). Cells treated 24 hours previously were analyzed for CD86, CD83, CD80, ICAM-1, MHC II (HLA-DR, HLA-DQ), and MHC I expression. While no changes in dendritic cells phenotype were observed when adenoviral was used alone, clear alterations including augmented expression of CD86, HLA-DR and HLA-DQ were observed with all three high efficiency adenoviral gene delivery systems. Unique features imparted by treatment with either Fab-anti-CD40 conjugate or CD40-targeted adenoviral included those changes most closely associated with dendritic cells maturation, namely increased expression of CD83 and ICAM-1.

Figure 6:
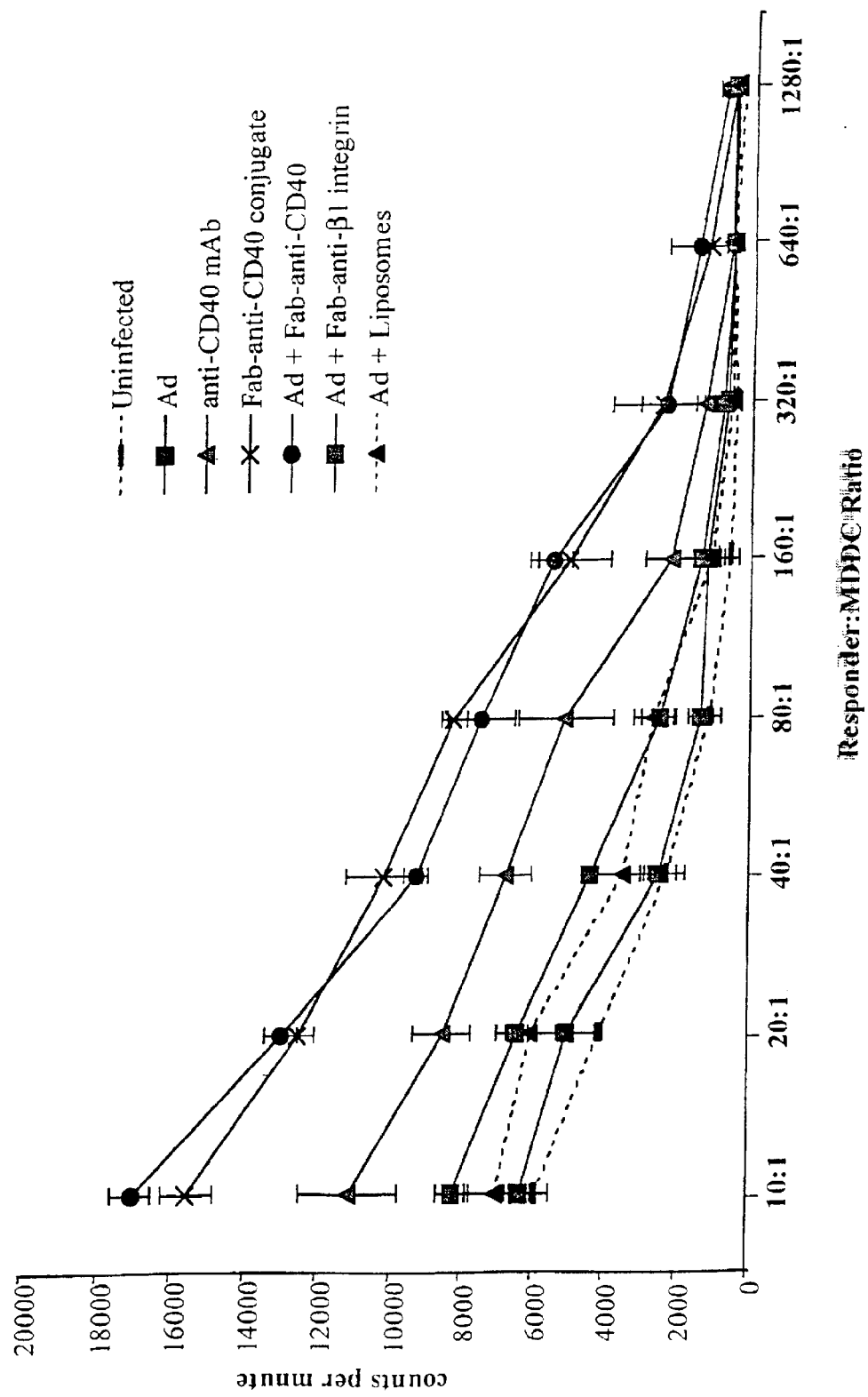
FIG. 6 shows that targeting to CD40 mediates enhancement in the capacity to generate an allo-Mixed Lymphocyte Reaction. Monocyte derived dendritic cells were treated with the indicated conditions and mixed with non-adherent lymphocyte responder cells MLR at the indicated Responder/Stimulator ratios (R:S). Cells were subsequently $^3$H labeled and assessed for cell associated cpm after 3 days.

A more rigorous index of dendritic cell maturation is the mixed lymphocyte reaction. Monocyte derived dendritic cells treated using several vectors or conjugates were combined with responder cells from an allogeneic donor and tested for the capacity to elicit responder cell proliferation. While adenoviral alone did not mediate enhancement in MLR, any treatments in the presence or absence of adenoviral were able to dramatically promote monocyte derived dendritic cell reactivity in the allo-MLR (FIG. 6). Moreover, while the effect of unconjugated mAb was significantly less than that seen with Fab-anti-CD40 conjugate in the presence of adenoviral, the effect of conjugate alone was comparable to that seen with the conjugate with virus. One possible explanation of the maturational effects observed with CD40-targeting could have been a viral-mediated effect from high efficiency entry of adenoviral particles into dendritic cells. For this reason, dendritic cells infected with the alternate high efficiency adenoviral vectors β1 integrin targeted adenoviral or liposome complexed adenoviral were also tested in an MLR. The failure of these alternate vectors to mediate notable enhancements suggests the maturation phenomenon is CD40-associated.

Figure 5:
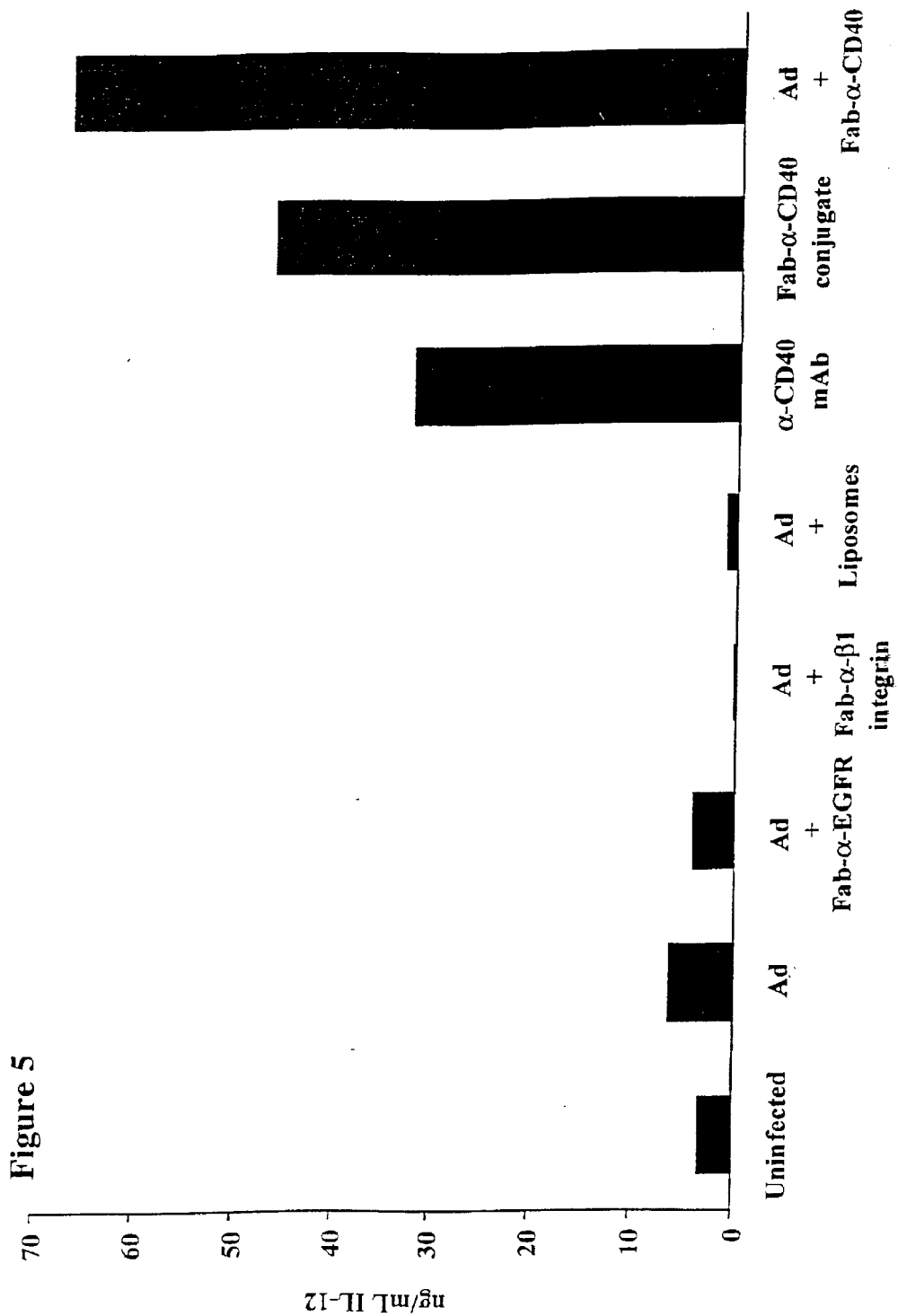
FIG. 5 shows that IL-12 production is enhanced after treatment with the anti-CD40 Ab or Fab-anti-CD40 targeting conjugate. Monocyte derived dendritic cells were treated with the indicated retargeted adenoviral or in the absence of adenoviral with unconjugated anti-CD40 Ab or the Fab-anti-CD40 conjugate. At 48 hours, the supernatants were assessed by ELISA for production of IL-12, a marker of dendritic cells maturation. Of note, values below 8 ng are beyond the linear range of detection by this assay.

As further evidence of functional maturation, monocyte derived dendritic cell supernatants were tested at 48 hours for production of IL-12, a cytokine for which expression is characteristic of dendritic cells maturation [Cella, M, et al. 1996. J. of Exp. Med. 184:747–52] (FIG. 5). The results indicated that IL-12 levels were dramatically augmented several fold in supernatants of cells treated with unconjugated G28.5 mAb and even higher with Fab-anti-CD40 retargeting conjugate alone or with CD40-retargeted adenoviral.

Discussion

Despite enormous clinical potential, widespread application of genetically modified dendritic cells has been hindered by several obstacles. Among these are the extensive handling required for ex vivo transduction, the poor gene transfer efficacy by existing vectors, and the necessity to mature dendritic cells to a immunologically potent state subsequent to gene transfer [Bancheareau and Steinman, 1998, Nature. 392:245]. Peripheral dendritic cells active in the process of antigen capture are referred to as "immature dendritic cells." In spite of active antigen retrieval, these cells do not express the appropriate panel of costimulatory molecules and cytokines necessary to activate effector cells such as cytotoxic T-lymphocytes (CTL's). As such, immature dendritic cells must be differentiated to an immunologically potent "mature" status by CD40 activation [Bennett et al., 1998, Nature. 393:478; Ridge et al., 1998, Nature. 393:474; Schoenberger et al., 1998, Nature. 393:478]. For this reason, the effects the CD40-targeted adenoviral vector have on the maturational status of dendritic cells were examined.

The ability of the anti-CD40 conjugate, and to a lesser extent monomeric antibody, to mediate dendritic cell maturation in the absence of virus clearly indicates that the maturation phenomenon is adenoviral-independent. Further, based on expression of CD83 and ICAM-1, production of IL-12 and improved MLR observed almost exclusively with treatment of dendritic cells by CD40 mAb, Fab-anti-CD40 conjugate, and CD40-targeted adenoviral but not with other adenoviral vectors tested, it seems fairly certain that this maturational phenomenon is a direct and specific result of targeting to CD40.

The present invention shows that retargeting adenoviral gene delivery to CD40 mediates dramatic increases in the magnitude of gene transfer and maturational effects that are specific for CD40. Consequently, despite the comparable enhancements of conjugate targeted adenoviral and liposome complexed adenovirus ex vivo, the more cell specific targeting and maturational potential of CD40-targeted adenoviral would, in theory, lend itself more reliably to in vivo approaches.

In sharp contrast to previous studies documenting increased CD40 expression upon dendritic cell maturation, in all cases using a CD40 mAb or CD40-based conjugate, FACS analysis revealed a reduction in surface CD40 expression at 24 hours. Since the conjugate has been detected on the cell surface at 48 hours after treatment, it is possible that the retained conjugate might have obscured subsequent detection of CD40.

The present invention shows that Fab-anti-CD40 conjugate mediates more dramatic MLR reactivity in monocyte derived dendritic cells than seen with unconjugated anti-CD40 monoclonal antibody. Previous reports implicate CD40 crosslinking as a means to activate the CD40 pathway and herein are proposed two means by which the present system has altered the crosslinking kinetics of this antibody. First, the inherent trimericity of the fiber-knob lends itself to binding of up to three conjugate molecules per each of twelve capsid vertices. Second is the semi-random nature of the chemical crosslinking procedure which can result in heterodimers with ratios besides a simple 1:1 Fab to anti-CD40 monoclonal antibody.

In summary, it appears that adenovirus mediates minor effects on dendritic cell phenotype, but these effects are seen only when a sufficient number of particles enter each cell, such as by the high efficiency antibody-targeted or liposome-complexed adenoviral based gene transfer vectors. It is interesting to speculate as to whether the enhanced expression of costimulatory molecules seen with $\beta 1$ integrin-targeted or liposome-complexed adenoviral is a consequence of the capsid itself entering the cell, expression of the transgene, or by background adenoviral gene expression. The dual role of CD40 in this scenario as both a surrogate adenoviral receptor and a powerful trigger of dendritic cell maturation will be useful as a retargeting strategy to this central cell type of the immune system.

One benefit of a CD40-retargeted adenoviral vector is that by delivery of an antigen-encoding gene, a larger pool of dendritic cells can be generated with the potential to prime effector cells against the antigen of interest, especially important in the case of cryptic antigens that might otherwise be inaccessible to the immune system. Stemming from the important role of CD40 in T-helper activation of dendritic cells, such a system might also have applications in bypassing the need for CD4+ T cell help in activation of CTL. While the utility of bispecific-antibody based targeting of adenovirus for clinical purposes has been previously suggested, the limitations of this antibody based strategy for intensive clinical applications has been recognized. For this reason, a genetic fusion strategy between the trimeric adenovirus fiber and the natural ligand of CD40, trimeric CD40L, is useful.

EXAMPLE 2

Transduction of B-Cells

Figure 7A:
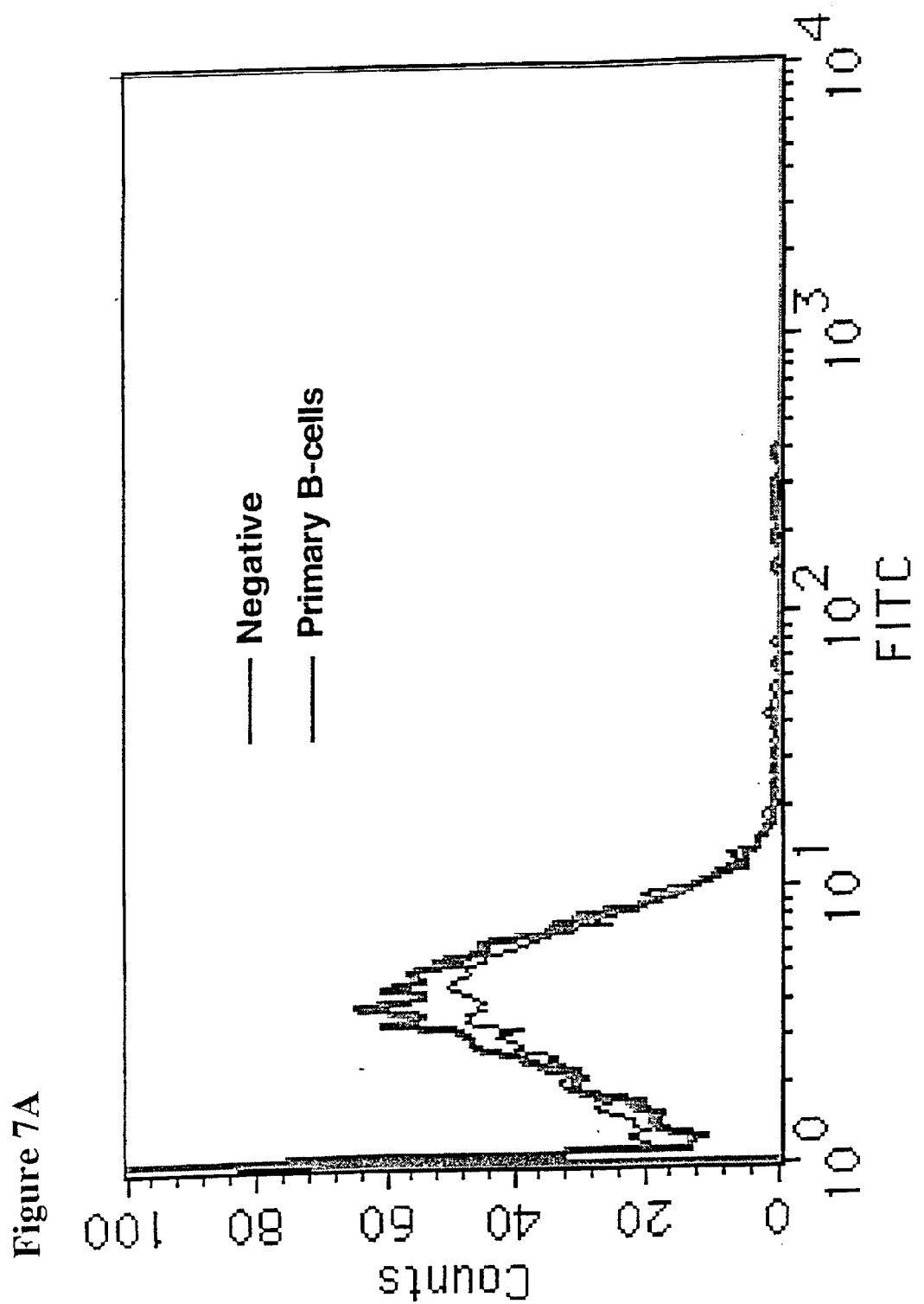
FIGS. 7A–7B show that primary B-cells are deficient in CAR (FIG. 7A) and the αv integrin, αvβ5 (FIG. 7B). The adenoviral entry receptors. Cells were FACS analyzed using the anti-CAR mAb RmcB and the anti-αvβ5 specific mAb P1F6. (analysis of αvβ3 was similar to αvβ5).
Figure 7B:
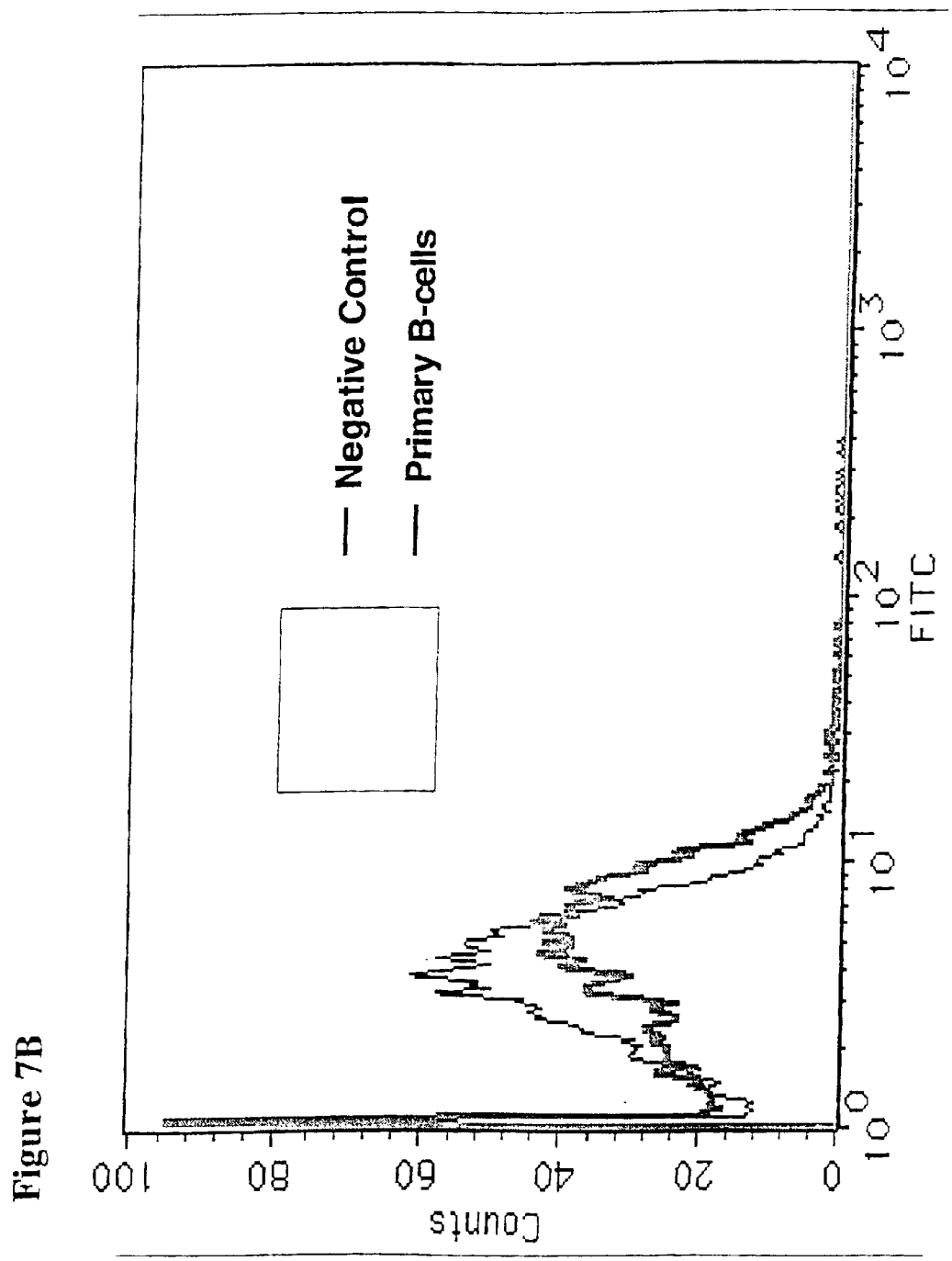

It has been recognized for quite some time that lymphocytes are a difficult cell type into which genes can be delivered. Several types of hematopoetic cells have been documented for their failure to mediate binding and/or internalization of adenoviral viral particles [Silver and Anderson, 1988, *J. Virology.* 62:341; Mentel et al., 1997, *J. Wed. Virology.* 51:252; Wattel et al., 1996, *Leukemia.* 10:171]. A failure of primary B-cells to express both the primary adenoviral receptor CAR and the secondary receptors, the $\alpha v$ integrins, has been recognized (FIGS. 7A & 7B). This would explain the failure of adenovirus to infect these cells effectively.

Figure 8:
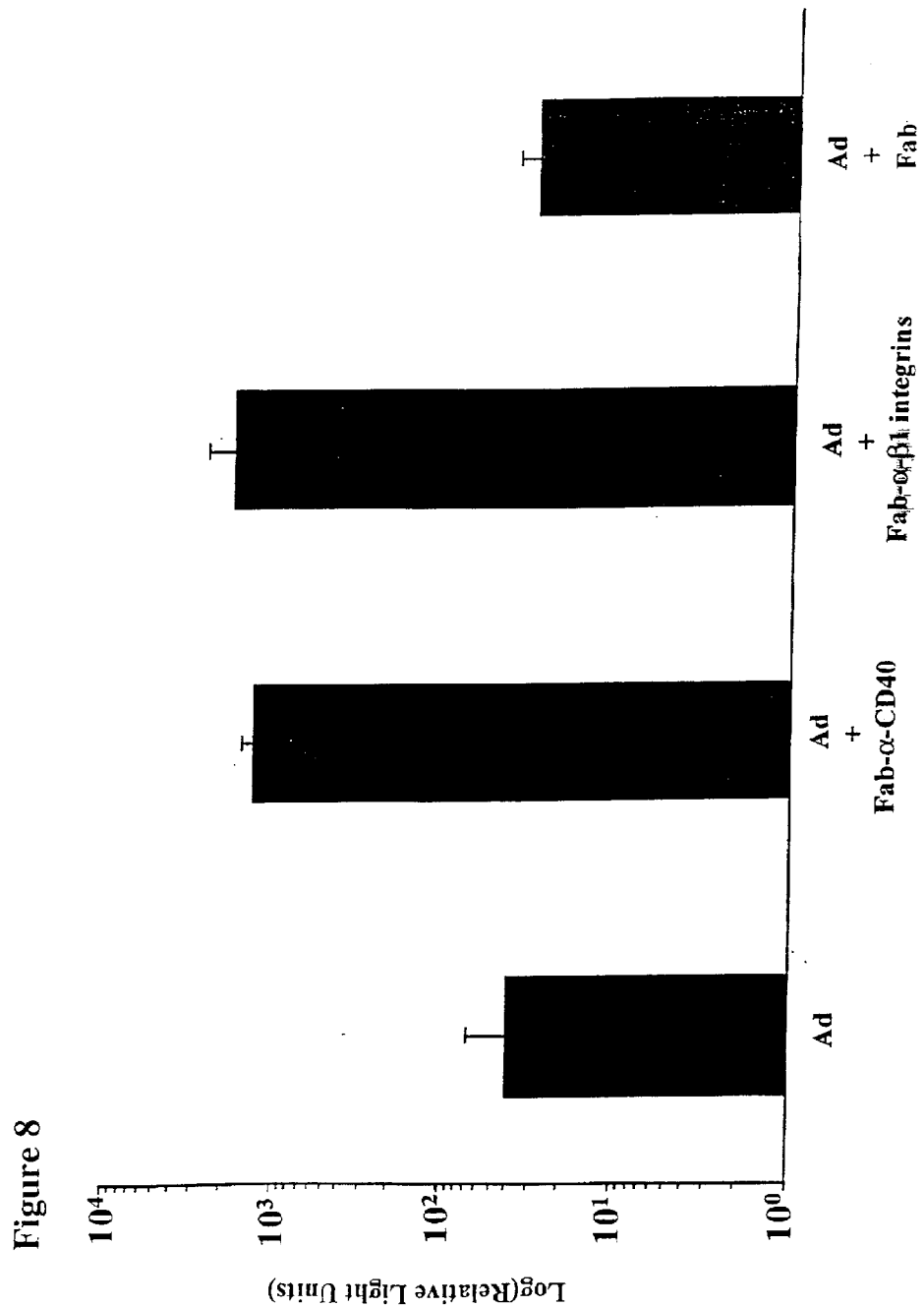
FIG. 8 shows that adenoviral targeted by Fab-anti-CD40 or Fab-anti-β1 integrins mediates enhanced magnitude of gene transfer to primary normal B-cells. Purified primary B-cells were infected with AdCMVLuc either alone or complexed the following as indicated Fab, Fab-anti-CD40, or Fab-anti-β1 integrins. After 24 hour incubation, cells were assessed for expression of luciferase.
Figure 9:
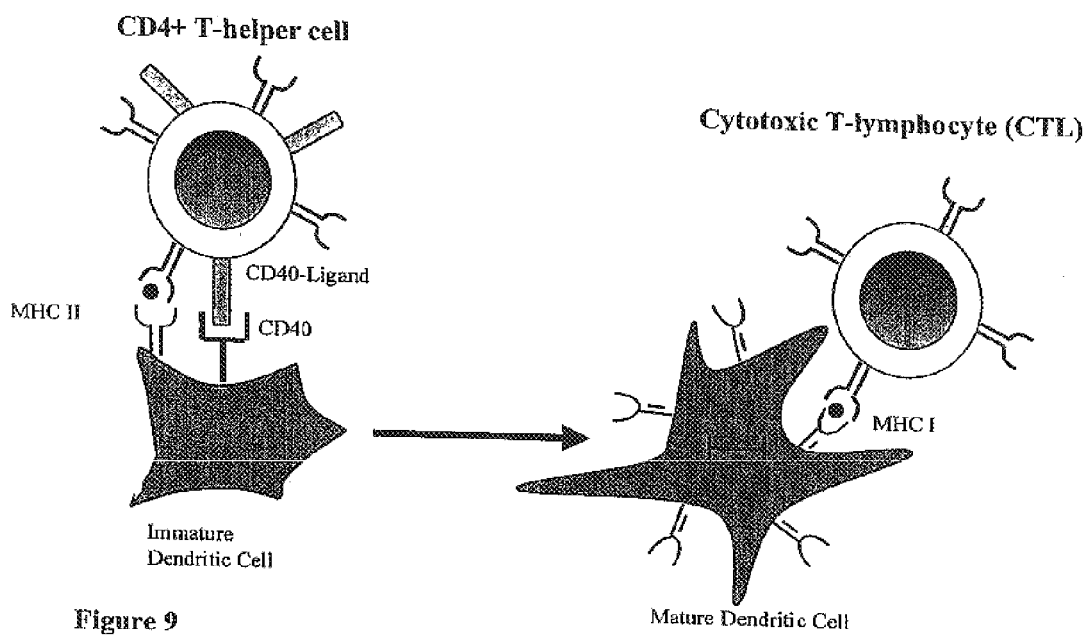
FIG. 9 shows that in nature, activation of dendritic cells is mediated by CD40-Ligand expressed on T-helper cells that enables maturation of dendritic cells such that they can properly stimulate cytotoxic T-lymphocytes (CTL's).
Figure 10:
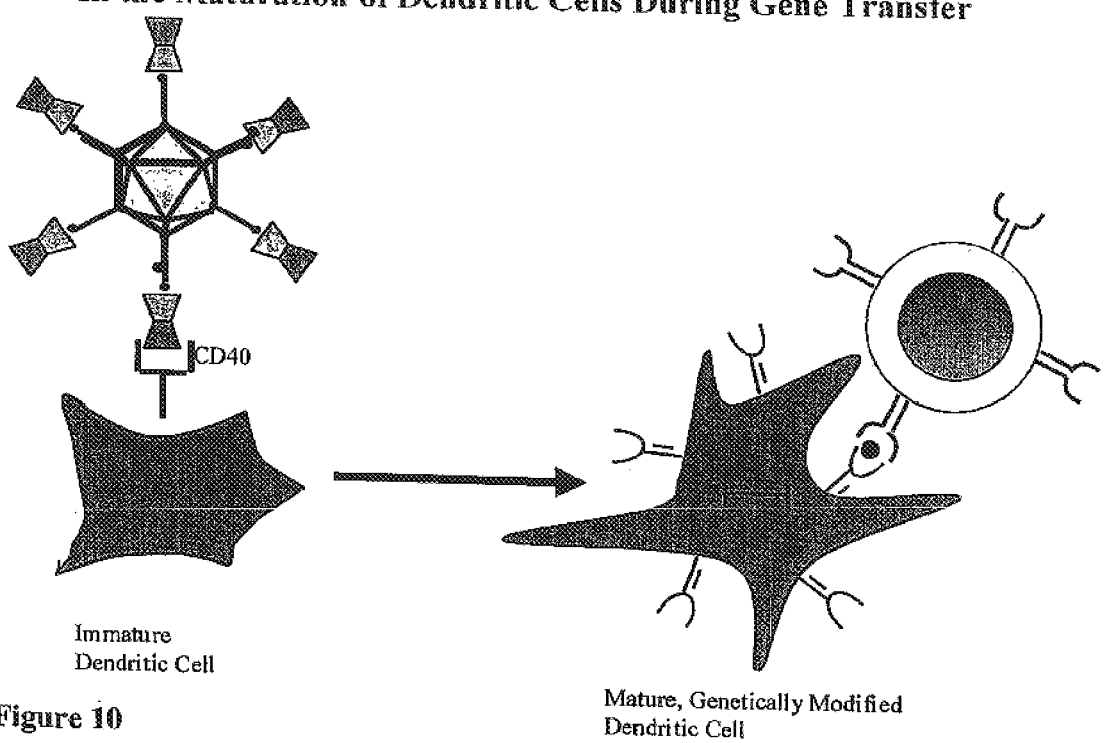
FIG. 10 shows that CD40-targeted adenovirus may substitute for CD4+ T-helper function through activation of CD40 leading to maturation of dendritic cells. For this reason, CD40-targeted adenoviral may enable stimulation of a CTL response even in the absence of functioning T-helper cells.

To overcome this deficiency, the conjugates Fab-anti-CD40 and Fab-anti $\beta 1$ integrins directed against the B-cell markers CD40 and the $\beta 1$ integrins, respectively, were used. Both of these conjugates were expected to reconstitute binding to replace the absence of CAR and to provide an alternative method for virion internalization into the cells. By virtue of the previously described internalizing function of these receptors, these conjugates were also anticipated to reconstitute the internalizing function of the $\alpha v$ integrins. By use of either of these retargeting strategies, gene transfer to primary B-cells has been enhanced by a least 10-fold over untargeted adenoviral (FIG. 8). These results are particularly interesting because targeting of adenoviral to CD40 or the $\beta 1$ integrins seems to have simultaneously overcome deficiency of both the primary binding receptor as well as the secondary, internalizing receptor.

EXAMPLE 3

CD40-Targeted Adenovirus Enhances Dendritic Cell Based Vaccination

Materials and Methods

Viruses and Cell Lines

Adenovirus carrying the gene for HPV E7 mutant in the pRb binding domain, indicated in the text as AdE7, was provided by Dr. Pradip Raychaudhuri (University of Illinois at Chicago) [Morozov et al., 1997, *J. Virol.* 71:3451]. The C3 tumor cell line (from Dr. Jan Ter Schegget, University of Amsterdam) was generated by transfecting C57BL/6 mouse embryonic fibroblasts with plasmids containing the entire genome of the human papillomavirus type 16 [Feltkamp et al., 1993, *Eur. J. Immunol.* 23:2242]. B16 melanoma cells were obtained from the ATCC (Manassas, Va.). Both C3 and B16 cells were cultured in DMEM supplemented with 4.5 g/L glucose.

CD40-targeting Conjugate

The anti-murine CD40 hybridoma FGK45 [Rolink, 1996, *Immunity* 5:319] was provided by Dr. Antonius Rolink (The Basel Institute for Immunology, Switzerland). The neutralizing murine hybridoma 1D6.14 specific for the carboxy-terminal, receptor binding knob domain of Ad serotype 5 fiber has been previously described [Douglas et al., 1996, *Nature Biotech.* 14:1574]. These hybridomas were used to generate hybridoma supernatants using Nutridoma (Boehringer Mannheim; Indianapolis, Ind.). Bispecific antibodies consisting of the 1D6.14 neutralizing anti-Ad knob Fab fragment and the anti-CD40 antibody were prepared by chemical cross-linking with N-succinimidyl 3-(2-pyridyldithio) propionate (SPDP) as previously described [Segal, et al., above]. The conjugate of FGK45 mAb and 1D6.14 Fab is henceforth designated as Fab-anti-murine CD40.

Assessment of Phenotypic Murine Dendritic Cell Maturation

For maturational analyses, Abs used were directly conjugated to FITC (Pharmingen, San Diego, Calif.). These included: 3E2 (anti-CD54), 16-10A1 (anti-CD80), GL1 (anti-CD86), AF6-88.5 (anti H-2K$^b$), AF6-120.1 (I-A$^b$), G155-178 95 (Mouse IgG isotype control), R35-95 (Rat IgG isotype control), and G235-2356 (Hamster IgG isotype control). Anti-CD40 mAb, FGK45, was detected by the FITC labeled goat anti-rat mAb (Jackson Immunoresearch Laboratories; West Grove, Pa.).

Bone Marrow Derived Murine Dendritic Cells

Bone marrow dendritic cells were prepared as described by Inaba (Inaba et al., 1992, *J. Exp. Med.* 176:1693]. Briefly, bone marrow was collected from femurs and tibias of 4–8 week old C57BL/6 mice. Bone marrow cells were incubated with a mixture of antibodies directed against B220 (clone RA3-3A1/6.1), CD4 (clone GK1.5), CD8 (clone 53-6.72), and Ia (B21-2) using exhausted supernatants from hybridomas (ATCC). Subsequently, cells were incubated with rabbit complement (Cedarlane, Ontario, Canada) to deplete contaminating lymphocyte populations. Remaining cells were cultured in RPMI containing 10% FCS and 100 U/mL recombinant murine GM-CSF (Peprotech; Rocky Hill, N.J.). After 6 days of culture, loosely adherent dendritic cells clusters were collected and replated in 100 mm dishes for 3 hours prior to infection. The purity of these dendritic cells was established by the absence of lineage markers in flow cytometry analysis.

Preparation of Targeted Adenovirus

Adenovirus was incubated for 30 minutes at room temperature with Fab-anti-murine CD40 at a ratio of 30 ng/2.4× $10^6$ plaque forming units (pfu) in complete RPMI containing 2.5% FCS. Adenovirus conjugated with Fab-anti-murine CD40 will be referred to henceforth as CD40-targeted adenovirus. For instances designated as untargeted adenovirus, virus was mock incubated with media containing no conjugate.

Infection of Murine Dendritic Cells for Assessment of GFP Gene Transfer

To assess the percent of dendritic cells transduced, cells plated in 6-well plates were infected with untargeted or CD40-targeted AdGFP at an MOI of 10, 100, or 1000 in the presence or absence of conjugate for exactly one hour at 37° C. before unbound virus was washed away with PBS. Cells were subsequently incubated in RPMI containing 10% FCS (RPMI 10%). Alternately, cells were incubated with a constant MOI of 100 for a duration of one, six, or twenty-four hours as indicated. After 24 hours of incubation, cells were analyzed by flow cytometry for expression of GFP.

Infection of Murine Dendritic Cells for Maturation Analysis and Immunizations

Adherent dendritic cells were incubated for exactly one hour at 37° C. under one of the following conditions: mock infection (dendritic cells), CD40-targeted AdLuc (40AdLuc), untargeted AdE7 (AdE7) or CD40-targeted AdE7 (40AdE7). Subsequently, cells were washed with PBS to remove unbound virus and RPMI 10% was added to each dish. After 24 hours pooled adherent and non-adherent cells were collected and used for either flow cytometry or vaccination.

Prophylactic Dendritic Cell Immunization

Mice were administered a primary vaccination intradermally equal to the number of dendritic cells indicated; one week later a booster vaccination equal to half the dose of the primary vaccination was administered. Specifically, cell concentration was adjusted such that a 200 µL injection would constitute the indicated number of cells. This volume was distributed between 4–5 vaccination sites on the animal. One week after the booster vaccination, mice were challenged with tumor cells.

Tumor Challenge

Cells were released from culture vessels with trypsin and washed twice in PBS. Subsequently, mice were injected subcutaneously on the right flank with either 2 million C3 or 20,000 B16 cells as indicated.

T cell Depletion

To deplete CD8+ T cells in vivo, mice were injected i.p. with 200 µg of purified mAb from the anti-CD8+ hybridoma 53-6.72 that had been purchased from the ATCC. Antibody was administered relative to the primary vaccination on days: −2, 1, 5, 10, 13, and 17. CD8+ depletion was validated by flow cytometry of splenic suspensions. On day 0 mice received a primary vaccination of 12,000 dendritic cells infected. Subsequently, on day 7, a booster vaccination of 6,000 dendritic cells was administered and on day 14 a challenge with 2 million C3 was given.

Pre-Immunization of Mice with Ad Infected Dendritic Cells

At 28 and 21 days prior to tumor challenge, mice were vaccinated with 25,000 and 12,500 dendritic cells infected by AdLuc, respectively for preimmunization to Ad. At 14 and 7 days before challenge, mice received primary and booster vaccinations of 12,500 and 6,250 dendritic cells, respectively, infected by either AdE7 o r CD40-targeted AdE7, as indicated.

Vaccination against Established Tumors

Tumors were established by subcutaneous injection of C3 cells three weeks prior to the first vaccination. Only mice bearing tumors with a minimal volume of 100 mm$^3$ at three weeks were advanced to therapeutic vaccination studies. Mice were size matched into four groups corresponding to a group of unvaccinated animals or those vaccinated with dendritic cells infected by CD40AdLuc (40AdLuc), AdE7, or CD40AdE7 (40AdE7). Mice were immunized with a dose of 200,000 dendritic cells in a total volume of 200 µL on each of four weekly vaccinations. In particular, mice were vaccinated at four to five sites distant from the tumor mass. Tumors were monitored for 15 weeks or until tumors had reached a volume of 1000 mm$^3$, at which point mice were euthanized.

Statistical Analysis

The chi-squared test was performed to analyze nominal data of tumor incidence from tumor protection experiments. The log rank-test was used to determine significance of therapeutic survival data in the Kaplan-Meier plot.

Retargeting of Ad to CD40 Increases Gene Transfer to Murine Dendritic Cells

A limited availability of efficient strategies to deliver antigen encoding genes to dendritic cells has hindered gene based dendritic cell vaccination strategies. Strategy of targeting of adenovirus to CD40 by means of bispecific antibodies was transitioned to a murine context to allow evaluation of vaccine efficacy in an appropriate model system. Briefly, an activating anti-CD40 antibody, FGK45, was chemically conjugated to a Fab fragment of an anti-adenoviral antibody, 1D6.14, to generate a bispecific targeting conjugate. To illustrate that adenovirus complexed with this conjugate, henceforth designated as CD40-targeted Ad, could enhance gene transfer to murine dendritic cells relative to untargeted adenovirus, delivery of the marker gene GFP by adenovirus was assessed by flow cytometry.

Figure 11:
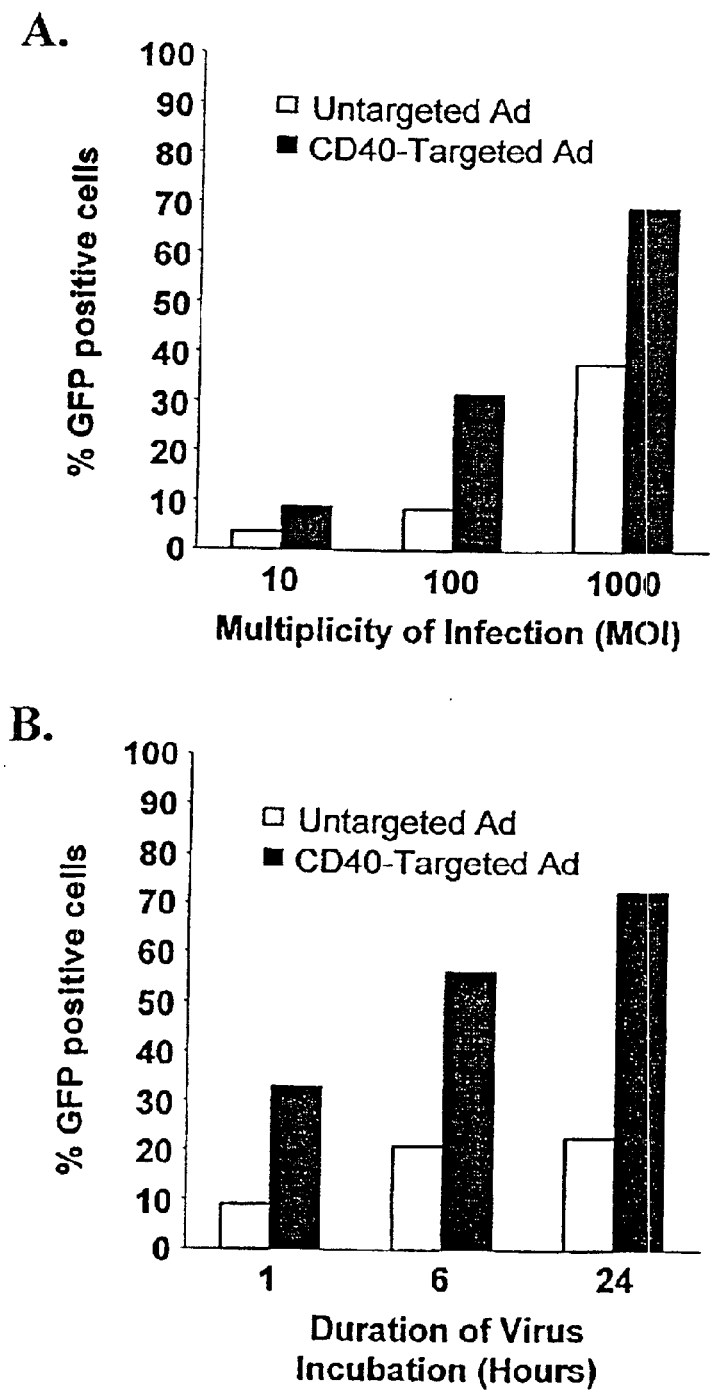
FIGS. 11A–11B show targeting of adenovirus to CD40 enhances the number of cells transduced relative to untargeted Ad. Murine bone marrow derived from dendritic cells were infected with AdGFP either alone or complexed with Fab-anti-CD40 for 1 hour at a multiplicity of infection (MOI) of 10, 100, or 1000 (FIG. 11A) and for 1, 6 or 24 hours at an MOI of 100 (FIG. 11B). After 24 hours of incubation, the samples were assessed for expression of GFP by flow cytometry. Results of representative experiments are depicted as percent of GFP-positive cells based on analysis of 10,000 cells.

As shown in FIG. 11A, CD40-targeted adenovirus demonstrated enhanced gene transfer relative to untargeted adenovirus at each multiplicity of infection (MOI) tested. At an MOI of 100, for instance, CD40-targeted adenovirus transduced 30% of cells, relative to only 8% of cells by untargeted adenovirus. Importantly these results reflect a strict one hour incubation period of virus with cells before unbound virus was washed away. In contrast to the finding of poor gene transfer with adenovirus in the absence of targeting, others have reported a high efficiency of gene transfer to dendritic cells by at similar dosage [Song et al., 1997, J. Exp. Med. 186:1247; Zhong et al., 1999, Eur. J. Immunol. 29:964]. To reconcile the findings with these reports, the possibility that more cells may be transduced following extended duration of viral incubation was examined.

As shown in FIG. 11B, extended exposure of cells to virus yielded a higher percentage of dendritic cells transduced. In this regard, through extended incubation of cells with virus, untargeted adenovirus transduced upwards of 20% of cells by 24 hours, yet CD40-targeted virus maintained a distinct and consistent advantage over untargeted adenovirus at all timepoints tested. These higher levels of gene expression following prolonged incubation with untargeted adenovirus may explain the findings reported by others. Collectively, these results illustrate that targeting adenovirus to CD40 increases the efficiency or gene transfer to murine dendritic cells relative to untargeted vector.

CD40-Targeted Ad Phenotypically Matures Murine Dendritic Cells

Figure 12:
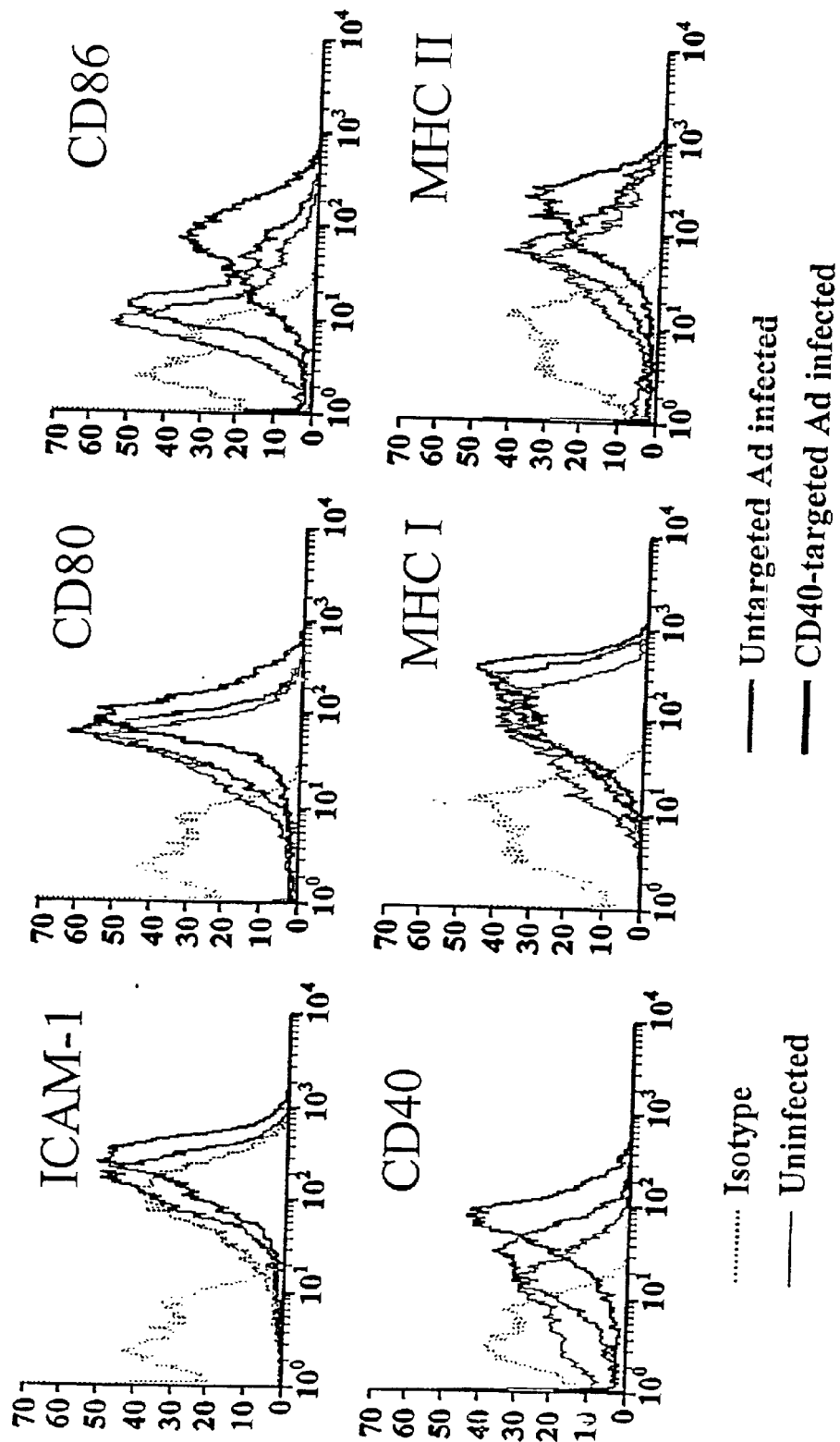
FIG. 12 shows that CD-40 targeting induces expression of dendritic cell maturational markers. Dendritic cells were infected with the vector indicated for 1 hour and subsequently incubated for 24 hours prior to analysis. Samples shown indicate expression of CD54, CD80, CD86, CD40, MHC I and MHC II. A total of 10,000 cells were counted per condition.

The essential role of maturity in the activation of T cells [Banchereau and Steinman. 1998, *Nature* 392:245; Mayordomo et al., 1997, *Stem Cells* 15:94] suggests that dendritic cells modified by a CD40-targeted adenovirus vector might have enhanced potential in the context of immunizations. To evaluate if a similar phenomenon accompanies targeting to murine CD40, dendritic cells which had been infected with untargeted adenovirus or CD40-targeted adenovirus were compared to uninfected cells by flow cytometry (FIG. 12). Relative to uninfected cells, cells infected by CD40-targeted adenovirus enhanced expression of several markers associated with dendritic cells maturation, particularly CD40, CD86 and MHC II. Minor changes were observed for cells infected with untargeted adenovirus, but these were less than that observed with CD40-targeted adenovirus. These findings indicate that targeting Ad to CD40 can mediate phenotypic changes that are associated with dendritic cells maturation.

Dendritic Cells Modified by CD40-Targeted Ad Exhibit Enhanced Vaccination Potential To establish the efficacy of adenoviral modified dendritic cells for immunization, the syngeneic C3 tumor model of HPV-induced neoplasms [Feltkamp et al., 1995, *Eur. J. Immunol.* 25:2638] was employed and a functionally mutated gene for the E7 antigen of HPV within an adenoviral vector, AdE7 [Morozov et al., 1997, *J. Virol.* 71:3451]. To assess the potential advantage of CD40-targeting of Ad in a vaccination context, a dose response curve was established to compare untargeted (AdE7) and CD40-targeted AdE7 (40AdE7) vectors.

Figure 13:
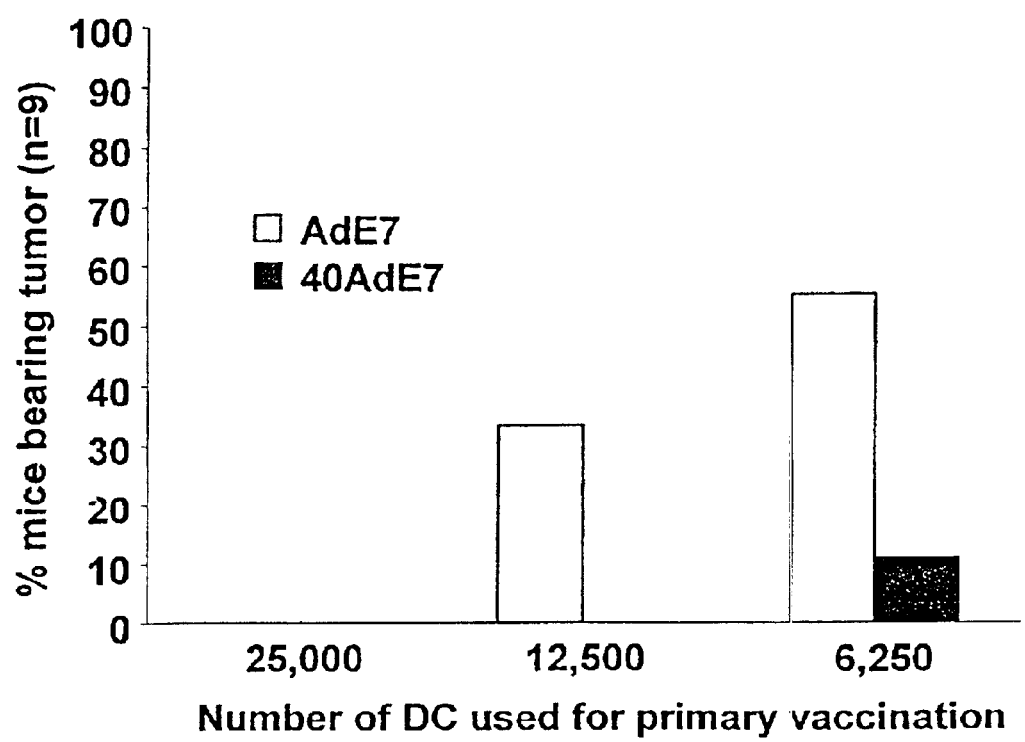
FIG. 13 shows dendritic cells infected by CD40-targeted adenovirus exhibit an advantage for in vivo vaccination over dendritic cells infected with untargeted adenovirus. Mice were vaccinated by intradermal injection of graded doses of dendritic cells infected by ether untargeted or CD40-targeted AdE7 (40AdE7) a s shown. On day-14, animals received a primary vaccination of 25,000; 12,500; or 6,250 dendritic cells as shown. Subsequently, on day-7 mice were given a booster vaccination equal to half the dose of the primary vaccination. On day 0, animals were challenged s.c. with 2 million C3 tumor cells. The percent of mice bearing tumors at 6 weeks post tumor challenge is shown in this representative experiment.

At a dose of 12,000 dendritic cells, for example, tumors had developed in animals vaccinated with dendritic cells transduced by untargeted AdE7 but not when CD40AdE7 had been employed (FIG. 13). Of note, among the tumors that did develop on mice in the lower dosage classes of E7 modified dendritic cells, the kinetics of tumor growth were slower than in mice which had been left unvaccinated. These findings suggest that dendritic cells modified to express tumor antigen by adenoviral vectors can mediate dose dependent prophylactic protection to tumor challenge and more importantly, that features of CD40-targeted Ad translate to an advantage for vaccination.

E7 Based Vaccination Is Antigen Specific

Dendritic cells impact the immune system through a number of antigen-nonspecific mechanisms. To establish that tumor protection was specific for E7 antigen two avenues were investigated. First a control vector (AdLuc), carrying the gene for an irrelevant antigen, luciferase was employed. Alternately a tumor line, B16 melanoma cells, negative for expression of the E7 antigen, was used in place of C3 cells for tumor challenge. As controls for nonspecific immune activation, dendritic cells were left uninfected or infected with CD40-targeted irrelevant vector AdLuc. Mice were vaccinated with dendritic cells infected with the indicated vector by a primary vaccination of 12,500 dendritic cells followed by a booster vaccination of 6,250 dendritic cells 7 days later. A week after the booster vaccination, mice were challenged with 2 million C3 tumor cells or 20,000 B16 cells, as shown.

Figure 14:
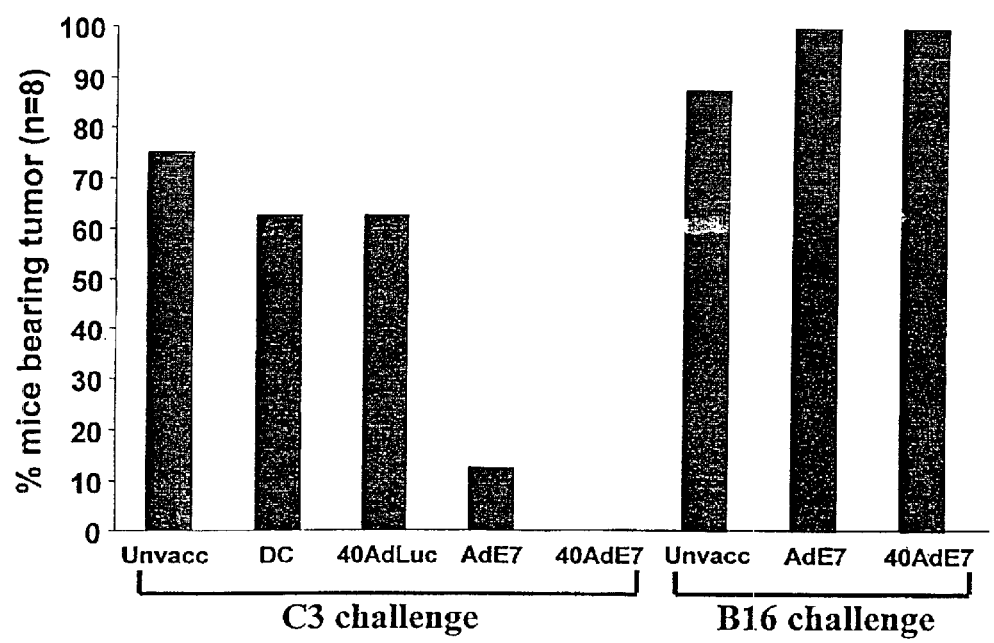
FIG. 14 shows dendritic cells genetically modified by adenoviral vectors elicit antigen specific immunity. Animals were left unvaccinated (Unvacc) or vaccinated by intradermal injection with dendritic cells infected as follows: mock infected (DC), infected by 40AdLuc, AdE7 or 40AdE7. Mice received a primary vaccination of 12,500 dendritic cells and a booster vaccination of 6,250 dendritic cells at 14 and 7 days prior to tumor challenge, respectively. One week following the booster vaccination, animals were challenged s.c. with 2 million C3 tumor cells. The percent of mice bearing tumors at 6 weeks is shown.

While unvaccinated mice developed C3 tumor masses, mice vaccinated with AdE7 transduced dendritic cells did not develop tumors (FIG. 14). Importantly, the baseline percentage of mice developing C3 tumors in unvaccinated mice is less than 100%, as reported previously [deBruijn and Schuurhuis, 1998, *Cancer Research* 58:724]. Notably, both unmodified dendritic cells and AdLuc transduced dendritic cells imparted minor but not significant protection against tumor development. Alternately, dendritic cells transduced with AdE7, whether targeted or not, were unable to protect mice from challenge with antigen disparate B16 melanoma. These findings illustrate that dendritic cells genetically modified by targeted adenovirus generate immunity that is antigen specific as defined by the transgene carried within the adenoviral vector.

Depletion of CD8+ T cells Abrogates Dendritic Cells Induced Immunity

Figure 15:
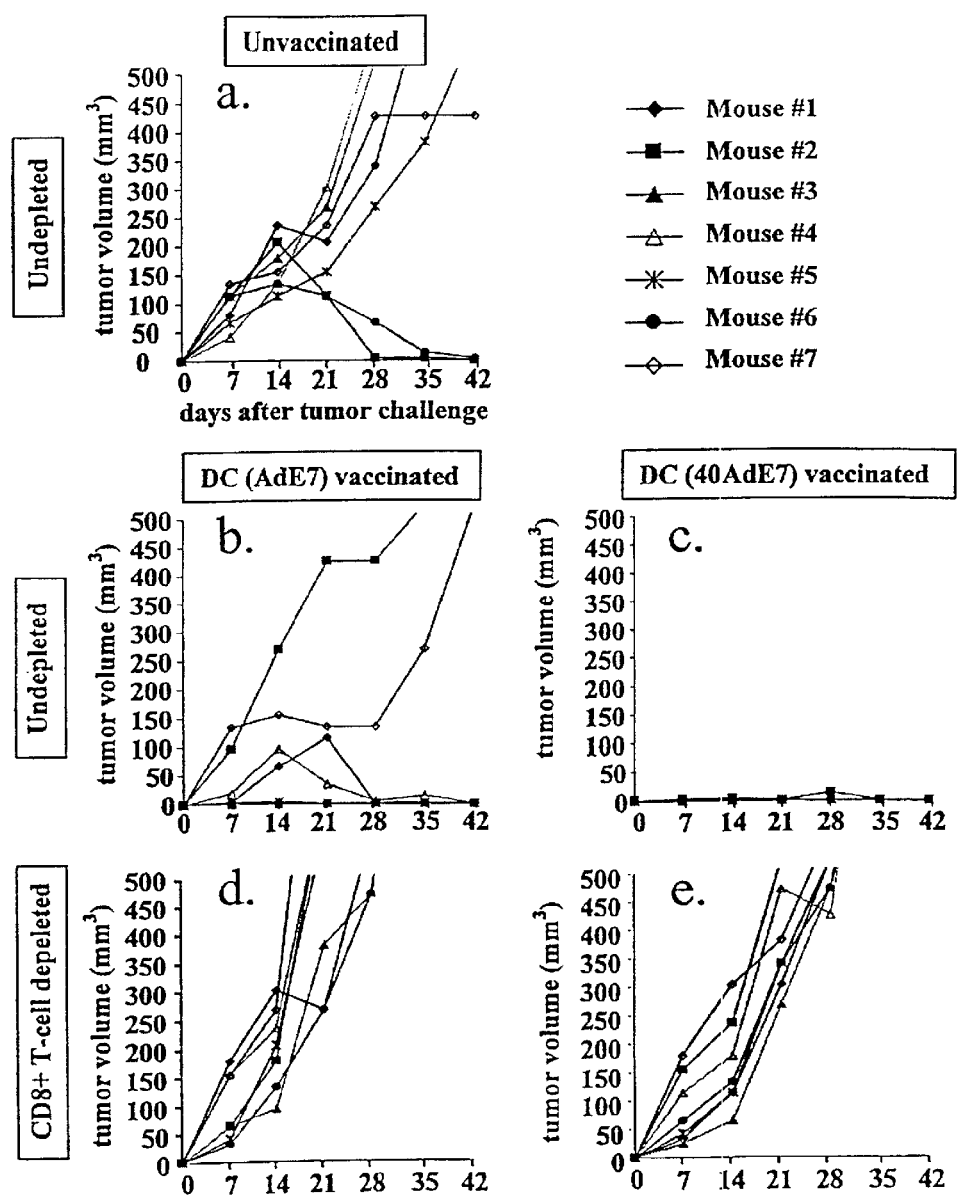
FIGS. 15A–15E show immunization with adenovirus modified dendritic cells is CD8+ T cell dependent. CD8+ T cells were depleted in vivo with mAb (FIGS. 15C and 15E). Mice were left unvaccinated (FIG. 15A), or immunized with dendritic cells previously infected by untargeted AdE7 (FIGS. 15B and 15C) or CD40AdE7 (FIGS. 15D and 15E) in primary and booster doses of 12,500 and 6,250 dendritic cells, respectively. Tumor growth per each condition is shown for 6 weeks after tumor challenge or until the tumor volume exceeded 500 mm$^3$.

T cells play a prominent role in tumor rejection and it is through T cells that dendritic cells are believed to mediate their effects on anti-tumor immunity [Pardoll, 1998, *Nature Med.* 4:525]. To investigate the role of CD8+ T cells in the tumor protection observed with this system, subsets of mice were depleted of CD8+ T cells during primary and booster vaccinations and subsequent tumor challenge with C3 tumor cells. While both AdE7 and 40AdE7 conferred protection to challenge in undepleted mice, depletion of CD8+ cells entirely compromised the anti-tumoral effects of E7-based vaccination (FIG. 15). Thus the findings confirm that the effector function of dendritic cells infected either by untargeted or CD40-targeted Ad is mediated through CD8+ T cells.

Pre-Immunization with Ad Infected Dendritic Cells Does Not Prohibit Dendritic Cells Based Vaccination Immune mediated clearance of adenovirus transduced cells has prompted concern over the utility of adenovirus as a gene therapy vector, especially for repeated administration [Jooss et al., 1998, *Gene Therapy* 5:309; DeMatteo et al., 1999, *Annals of Surgical Oncology* 6:88; Petrof et al., 1996, *Human Gene Therapy* 7:1813]. To examine the potential that adenoviral transduced dendritic cells may compromise subsequent administrations, mice were pre-immunized by primary and booster vaccinations of dendritic cells infected by adenovirus carrying a gene for an irrelevant antigen, luciferase. Subsequently, mice were administered primary and booster vaccinations of AdE7 transduced dendritic cells at one and two weeks following pre-immunization, respectively. To enhance the stringency of this pre-immunization, the doses of dendritic cells in primary and booster vaccinations for AdLuc infected dendritic cells were twice the doses of subsequent E7 modified dendritic cells. One week after the final immunization, mice received a tumor challenge with C3 cells.

Figure 16:
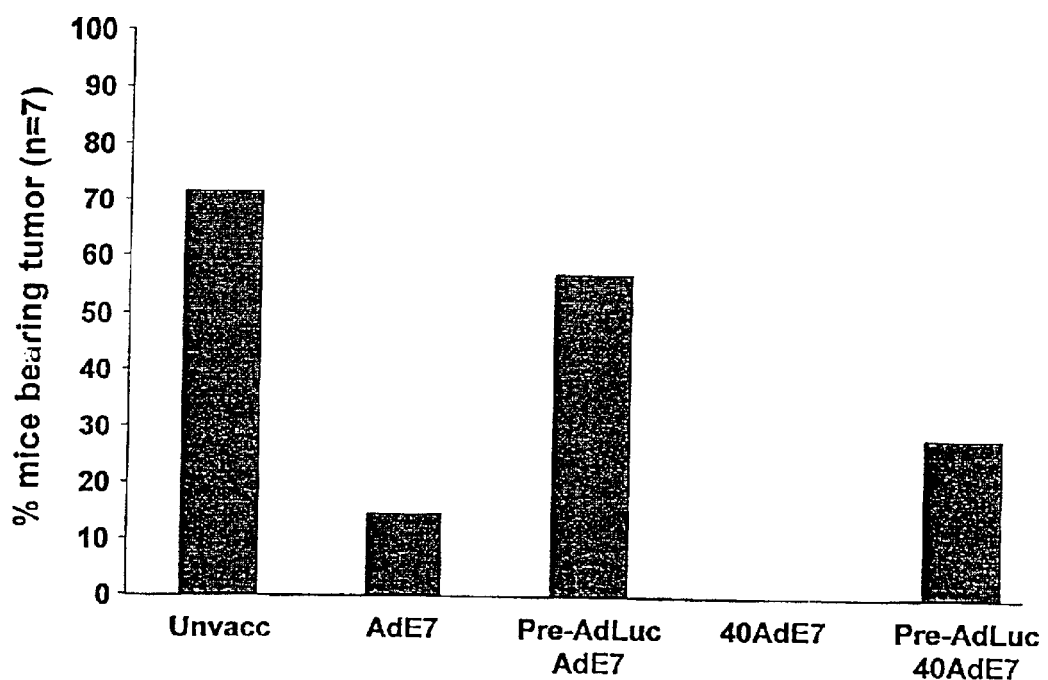
FIG. 16 shows preimmunization with adenovirus infected dendritic cells marginally reduces the efficacy of adenovirus modified dendritic cells vaccines. Mice designed with the prefix "PreLuc" received a primary prevaccination of 25,000 AdLuc infected dendritic cells and a booster of 12,500 AdLuc infected dendritic cells at 28 and 21 days prior to tumor challenge. At 14 and 7 days prior to tumor challenge, mice received vaccinations of 12,500 and 6,250 dendritic cells, respectively, infected with either AdE7 or 40AdE7, as indicated. Mice were challenged s.c. with 2 million C3 cells. The percentage of mice bearing tumors is shown at 6 weeks after tumor challenge.

In mice vaccinated with 40AdE7 infected dendritic cells, preimmunization with AdLuc infected dendritic cells resulted in tumor growth in 30% of animals, relative to complete protection in mice that had not been preimmunized (FIG. 16). These findings suggest that dendritic cells may be administered on multiple occasions and yet still provide protection in a significant percentage of preimmunized animals.

Dendritic Cells Modified by Targeted Ad Extend Survival of Mice with Pre-Established Tumors The initial goal of dendritic cell-based vaccinations in humans will likely be therapeutic, rather than prophylactic. The capacity of adenoviral modified dendritic cells to mediate regression of sizeable established tumors was evaluated in the murine model. Anticipating a more stringent challenge than prophylaxis, a larger vaccination dose was administered to elicit therapeutic immunity. Tumor-bearing mice remained unvaccinated or were administered four equivalent doses of 200,000 Ad modified dendritic cells spaced at weekly intervals with dendritic cells that had been infected by CD40-targeted AdLuc, untargeted AdE7 or CD40-targeted AdE7, as indicated.

Figure 17:
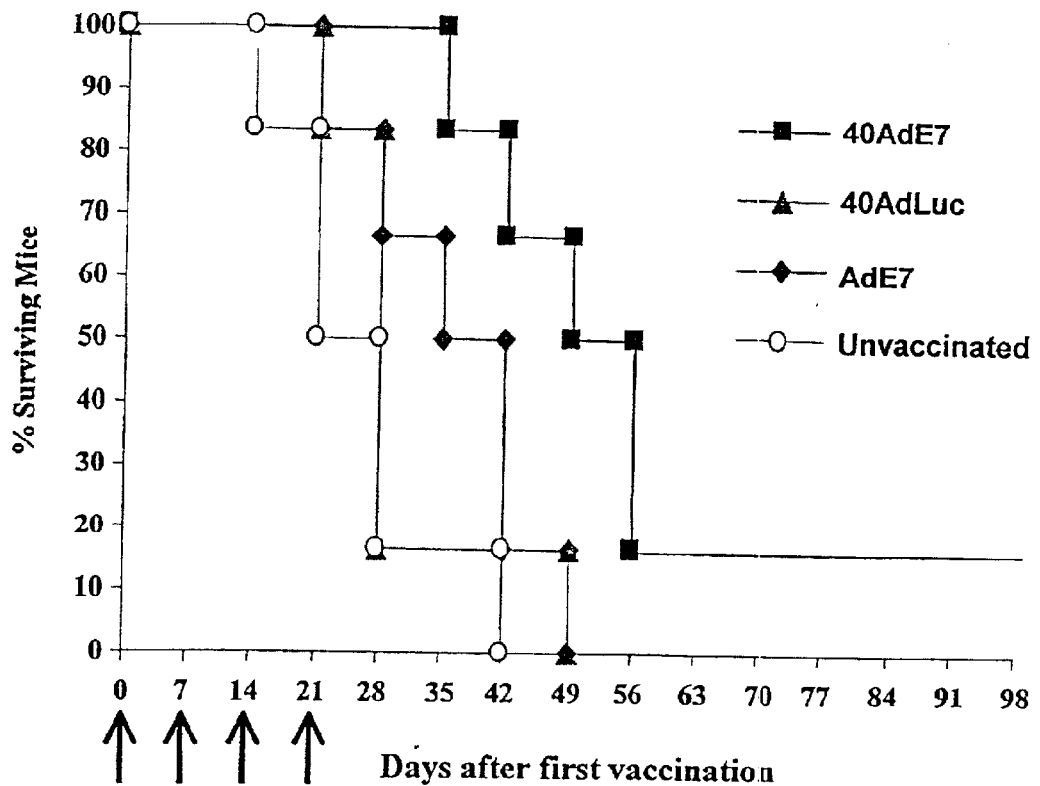
FIG. 17 shows dendritic cells infected with AdE7 can mediate therapeutic tumor immunity to extend survival of animals with pre-established tumors. Groups of animals bearing size matched established C3 tumors were left unvaccinated or immunized with dendritic cells infected by 40AdLuc, AdE7, or 40AdE7, as indicated. Four weeks vaccinations of 200,000 dendritic cells (indicated by arrows) were administered intradermally. The percent of surviving mice are shown until 14 weeks. Mice were euthanized when their tumors grew larger than 1000 mm$^3$ to avoid unnecessary suffering.

As shown in FIG. 17, relative to unvaccinated animals, mice vaccinated with dendritic cells infected by CD40-targeted AdE7 were able to significantly delay continued growth and ultimately extended survival relative to unvaccinated animals. In contrast, tumor growth in mice vaccinated with AdLuc transduced dendritic cells was not significantly distinct from unvaccinated animals. These findings confirm that genetically modified dendritic cells can initiate an antigen-specific therapeutic immune response against E7.

The potential utility of genetically modified dendritic cells is evidenced by their proposed applications in the treatment of infectious diseases, autoimmunity, allotransplantation, and cancer [Bancherau et al., 1998, Nature 392:245; Lotze et al., 1999, In Dendritic Cells: Biology and Clinical Applications. M. T. Lotze, and A. W. Thomson, eds. Academic Press, San Diego.] A significant hurdle to large scale application of therapies using dendritic cells will be a means by which to efficiently deliver antigen encoding genes to these cells. The poor infection of human dendritic cells can be explained by a deficiency of the adenovirus binding receptor [Tillman et al., 1999, J. Immunol. 162:6378]. To exploit the expanding role of CD40 in dendritic cell function [Grewal et al., 1997, Immunologic Research 16:59; Bennett et al., 1998, Nature 393:478; Ridge et al., 1998, Nature 393:474; Schoenberger et al., 1998, Nature 393:480] as an alternate adenovirus binding strategy, the present invention coupled a CD40 activating antibody with adenoviral vectors to achieve high efficiency dendritic cell vectors that target adenovirus vectors to CD40 on murine bone marrow-derived dendritic cells and explored the utility of this approach in antigen-specific vaccination.

Ad vectors targeted to CD40 consistently demonstrated a greater magnitude of gene transfer relative to untargeted adenovirus. Results shown above reveal that untargeted Ad tranduces a mere 8% of murine DC at an MOI of 100; these findings are consistent with those of several reports [Brossart et al., 1997, J. Immunol. 158:3270; Melero et al., 1999, Gene Therapy 6:1779]. In contrast, some investigators describe transduction efficiencies upwards of 90% using a similar dose of untargeted virus [Song et al., 1997, J. Exp. Med. 186:1247; Zhong et al., 1999, Eur. J. Immunol. 29:964]. To this end, it has been previously illustrated that upwards of 80% of virions can localize to a cell's nucleus within 60 minutes of infection [Leopold, 1998, Human Gene Ther. 9:367]; thus it would seem that gene transfer which occurs on a longer timescale does so inefficiently. On these grounds, a stringent one hour infection period was chosen in this study as a measure of rapid and efficient cell infection. To reconcile the above findings with those of others, it is reasoned that by extended exposure of DC to adenovirus, higher levels of gene transfer might be achieved. In a comparison of different durations of adenovirus incubation, it is found that at 24 hours 20% of cells were transduced by untargeted adenovirus, which still falls short of the 90% reported by others. Nevertheless, these results do suggest that, much like the importance of the dose of virus used, the duration of incubation between virus and cells is an important, yet often unreported, parameter.

The duration of incubation is perhaps inconsequential for ex vivo modification of dendritic cells. Nevertheless, the practical advantages of ultimate in vivo dendritic cell transduction are promising, especially in light of recent data suggesting that Ad targeted to CD40 can selectively transduce Langerhans cells of human skin. Accordingly, in vivo vaccination would eliminate the necessity for ex vivo manipulations to dendritic cells, further increasing the ease and flexibility of this approach. High efficiency vectors will become increasingly important because the duration of exposure of cells to injected virus may be limited under in vivo conditions. Perhaps most important, a high efficiency targeted Ad vector might have a distinct advantage in reducing the viral dose used in dendritic cell infection. Therein, the reduction of input viral dose may serve to minimize dose related toxicity associated with Ad vectors [Marshall, 1999, Science 286:2244; Nielsen et al., 1998, Human Gene Ther. 9:681; Newman et al., 1995, J. Clin. Investig. 96:2955; Schulick et al., 1995, Circulation 91:2406; Crystal et al., 1994, Nature Genetics 8:42].

The present invention also provides evidence of phenotypic maturation in murine DC infected by CD40-targeted Ad relative to untargeted Ad; a finding not unexpected given the CD40-activating capacity of the anti-CD40 mAb that was used in the targeting conjugate, FGK45 [Bennett et al., 1998, Nature 393:478; Schoenberger et al., 1998, Nature 393:480; Diehl et al., 1999, Nature Medicine 5:774]. Clearly, CD40-activation need not necessarily occur in the context of an adenoviral vector to mediate significant changes in DC phenotype and function. In fact, CD40 activation has been shown to potentiate any number of vaccination modalities [Diehl et al., 1999, Nature Medicine 5:774; Gurunathan et al., 1998, J. Immunol. 161:4563]. For gene based immunotherapy approaches, however, targeting Ad to CD40 can simultaneously increase much needed gene transfer efficiency of Ad vectors, with the prospective upshot of enhancing Ag presentation through DC maturation.

To establish if dendritic cells modified ex vivo imparted an advantage in vivo, the vaccination potential of dendritic cells infected by untargeted and CD40-targeted Ad vectors were compared using a murine model of cancers transformed by the human papillomavirus. Specifically, the present invention shows that Ad targeted to CD40 performed with greater prophylactic vaccination efficacy relative to untargeted Ad and in an antigen-specific manner. These findings, however, do not indicate whether enhanced gene transfer or CD40-induced maturation is predominately responsible for the observed enhancements in vaccination performance.

Apprehension over the delivery of entire coding regions for oncogenes have prompted the employment of peptide loading approaches for dendritic cell-based vaccinations [Mayordomo et al., 1997, Stem Cells 15:94; Lotze et al., 1999, In Dendritic Cells: Biology and Clinical Applications. M. T. Lotze, and A. W. Thomson. eds. Academic Press, San Diego], and among these have included approaches directed towards HPV-E7 [Diehl et al., 1999, Nature Medicine 5:774; Toes et al., 1997, Proc. Natl. Acad. Sci. 94:14660; Vierboom et al., 1998, J. Immunotherapy 21:399; Mayodormo et al., 1995, Nature Med. 1:1297]. Nevertheless, the clinical application of peptide loading is likely to be encumbered by issues of practicality. Widespread application of allele restricted peptides is limited in a human population with heterogenous MHC alleles and further by the narrow range of epitopes provided by individual peptides [Ressing et al., 1999, Eur. J. Immunol. 29:1292]. Such limitations are likely to be obviated through the employ of gene based modification of dendritic cells. By delivery of the E7 gene in its entirety dendritic cells can present from among a vast array of potential epitopes that are appropriate for the MHC alleles of the recipient. The basis of E7 oncogenicity has been defined [Mansur et al., 1993, *Biochim. Biophys. Acta* 1155:323; Phelps et al., 1992. *J. Virol.* 66:2418] and thus the present invention employes a mutant rendered functionally inoperative in its oncogenic pRb binding domain [Morozov et al., 1997, *J. Virol.* 71:3451]. It is also important to recognize that E7 expression alone is not sufficient for malignancy [zur Hausen, 1991, *Virology* 184:9] and further, that transformation is dependent upon continuous expression of E7 [Crook et al., 1989, *EMBO* 8:513]. The latter, in particular, is unlikely given the short-lived expression by Ad vectors. Thus, in the context of the proper vector and with proper functional deletions to the gene of interest, the use of vector delivered oncogenes need not necessarily be viewed with skepticism.

Legitimate concerns have been raised about the utility of Ad vectors in a population which has been previously exposed to adenovirus [Monahan et al., 1999, *Curr. Opin. Molec. Ther.* 1:558; Schmitz et al., 1983, *Am. J. Epidemiol.* 117:455]. Indeed, anti-Ad cellular immune responses have been recognized to severely compromise the duration of gene expression [Jooss, 1998, *Gene Therapy* 5:309; Petrof, 1996, *Human Gene Therapy* 7:1813; Yang, 1996, *Human Molec. Genetics* 5:1703; Yang, 1996, *J. Virol.* 70:7209]. In particular, Jooss et al. have shown that anti-Ad immune responses are a consequence of Ad transduction of DC [Jooss, 1998, *Journal of Virology* 72:4212]. In this regard, it would seem that DC intentionally modified by adenoviral vectors would paradoxically serve as the vehicle for their own destruction. In contradiction to this presumption, however, several studies have highlighted the utility of Ad infected DC for vaccination despite prior immunization with infectious Ad particles [Brossart, 1997, *J. Immunol.* 158:3270; Kaplan, 1999, *J. Immunol.* 163:699]. It is reasoned that rather than isolated Ad particles, pre-immunization with Ad infected DC would more rigorously test the capacity of Ad infected DC for repeated administration. The present findings reveal that pre-immunization with Ad infected DC does indeed decrease the immunization potential of subsequent DC vaccinations, yet a majority of mice still exhibit protection to tumor challenge. Several features might explain this counterintuitive finding. Foremost, adenoviral transgene expression in immunocompetent animals has been reported for at least 7 days prior to immune clearance [DeMatteo, 1999, *Annals of Surgical Oncology* 6:88]. By comparison, the timeframe for both migration of DC to lymphoid organs and interaction of DC with T cells occurs much more rapidly [Iezzi, 1998, *Immunity* 8:89; Ingulli, 1997, *J. Exp. Med.* 185:2133]. Further to this end, it has been established that DC undergo apoptosis after interaction with T cells [Matsue, 1999, *J. Immunol.* 162:5287]; thus it would seem that long term expression of antigens is not requisite for initiation of a productive immune response. It is hypothesized that activation of T cells by Ad infected dendritic cells may fall within a window prior to immune clearance of infected cells. While the present studies cannot conclude that repeated administrations will remain efficacious indefinitely, they do suggest that dendritic cells modified by Ad might be administered in a series of boosters without entirely compromising their effectiveness. In this regard, the high efficiency of CD40-targeted Ad may serve to reduce the magnitude and/or number of doses of dendritic cells necessary to attain a desired protective immunity before anti-Ad immune responses become insurmountable. For most gene therapy strategies, where long term expression is indispensable, the fleeting expression of a transgene by adenoviral vectors is a conspicuous disadvantage. For dendritic cell based immunizations, however, it would seem that even transient antigen presentation can effectively generate immune responses which would then be rendered enduring not by the dendritic cell, but presumably through memory T cells.

The earliest applications of dendritic cell based therapy will likely be therapeutic in nature. Despite the importance of cancer vaccines in this role, the effectiveness of other E7 based approaches in sizeable established tumors has not been rigorously demonstrated. In the present invention, mice bearing palpable pre-established tumors were vaccinated with dendritic cells infected by Ad carrying the gene for E7 or an irrelevant antigen. The results indicate that despite a significant prolongation in survival in animals vaccinated with dendritic cells modified by CD40-targeted AdE7, a vast majority eventually succumb to the tumor. Several possible mechanisms might explain the failure of E7 based vaccination to mediate complete tumor regression. Foremost, the extended survival suggests that an immune response is initiated, but subsequently compromised or otherwise rendered ineffective. In particular, the tumor cells used in these experiments were not maintained under a selective pressure. It possible that subpopulations of these cells did not express the E7 tumor antigen; alternately, these cells may have undergone an "immunological escape" in vivo, much as human tumor cells tend to do [Pardoll, 1998, *Nature Med.* 4:525]. These findings suggest that an optimal vaccine will potentially incorporate several antigen genes within a single vector, thus minimizing the potential for such escape.

In summary, the results indicate that Ad targeted to CD40 represents a high efficiency, dendritic cell potentiating gene delivery strategy that enhances the efficacy of DC based immunotherapy strategies in an antigen-specific manner. Further, Ad transduced dendritic cells may be administered in a limited number of repeated doses without compromising vaccine efficacy.

EXAMPLE 4

CD40-Targeted Adenoviral Gene Transfer to Human Cutaneous Dendritic Cells in situ Directly transfected dendritic cells (DC) have been shown to be responsible for the generation of specific T cell responses subsequent to genetic vaccination in the skin. Transduction of other non-professional antigen presenting cells may lead to T cell tolerance. The aim of the present study was therefore to use the CD40 targeting system described above to achieve selective transduction of cutaneous DC in situ.

Administration of untargeted Ad led to the expression of βGal in large numbers of cells in the dermis with less than 0.1% of these consisting of $CD1\alpha^+$ DC. By contrast, injection of CD4-targeted Ad resulted in a 100-fold reduction of the absolute number of transduced cells in the dermis with over 50% of these consisting of $CD1\alpha^+$ DC. These cells retained their capacity to migrate out of the dermis, as observed in a 48-hour migration assay.

Human Skin Explants

The culture medium used throughout was Iscove's modified Dulbecco's medium (GIBCO Laboratories, Paisly, Scotland) supplemented with 50 U/ml penicillin-streptomycin, 1.6 mM L-glutamine, 0.01 mM β-mercaptoethanol, and 5% pooled, complement-inactivated normal human serum (CLB, Amsterdam, The Netherlands). GM-CSF (Schering-Plough, Madison, N.J.) diluted in RPMI medium (GIBCO Laboratories, Paisly, Scotland) without supplements was used for intradermal injection. Human skin was obtained from patients undergoing corrective breast or abdominal plastic surgery. The skin specimens were placed with the epidermal side up and 100 ng GM-CSF was injected with a 0.2 mm needle into the dermis. At the injection site a 5 mm urtica appeared and a punch biopsy of 6 mm was taken exactly from this site. The biopsy was lifted from the specimen with a forceps and with scissors the dermis was cut at a depth of approximately 2 mm. Skin explants were cultured at air-liquid interface with the epidermal side up in a 6 well culture plate (Nunclon Delta, Intermed, Denmark) on sterilized stainless steel grids covered with a filter (Millipore 0.45 um) at 37° C. in 5% $CO_2$-containing humified air. At the indicated time points the explants were harvested, snap-frozen and stored in liquid nitrogen. Cryostat sections of 4 um were cut and placed on poly-L-lysine-coated slides, acetone-fixed for 10 min, pre-incubated with normal rabbit serum (1:20, CLB, Amsterdam, The Netherlands) for 10 min, and incubated for 1 hour with primary monoclonal antibodies directed against CD1α (1:20, Immunotech, Marseille, France), CD40 (1:100, Serotec, Oxford, UK), or with appropriate isotype control antibodies. Subsequent incubation with rabbit anti-mouse-biotin conjugate (1:150, DAKO, Glostrub, Denmark) for 30 min was followed by incubation with horseradish peroxidase-streptavidine complexes (1:500, DAKO, Glostrub, Denmark). Staining was then visualized with 3-amino-9-ethyl-carbazol (ICN Biochemicals, Aurors, Ohio) in the presence of hydrogen peroxide. Slides were counterstained with haemotoxylin and mounted. Two investigators independently counted stained cells in ten 400×-magnification fields. Positive cells in the skin sections were enumerated in ten epidermal and ten dermal fields.

For phenotypic analysis of the β-Gal positive cells cryostat sections were incubated for 10 min with 10% normal human pooled serum followed by CD1α-PE (Immunotech, Marseille, France) or IgG1-PE-isotype (Becton Dickinson, San Jose, Calif.) for 60 min, followed by visual inspection under a fluorescence microscope. Two investigators independently counted stained cells in ten 400×-magnification fields of the dermis.

Migration Assay

For migration assay the skin explants (12 samples per condition) were placed directly in culture medium with epidermal side up in a 48 well culture plate and the medium containing migrated cells was harvested and pooled after 48 hours. Cytospins were made and stained cells were counted in ten 400×-magnification fields by two independent observers.

Expression of CD1α and CD40 in Epidermis and Dermis of Skin Explants

Figure 18A:
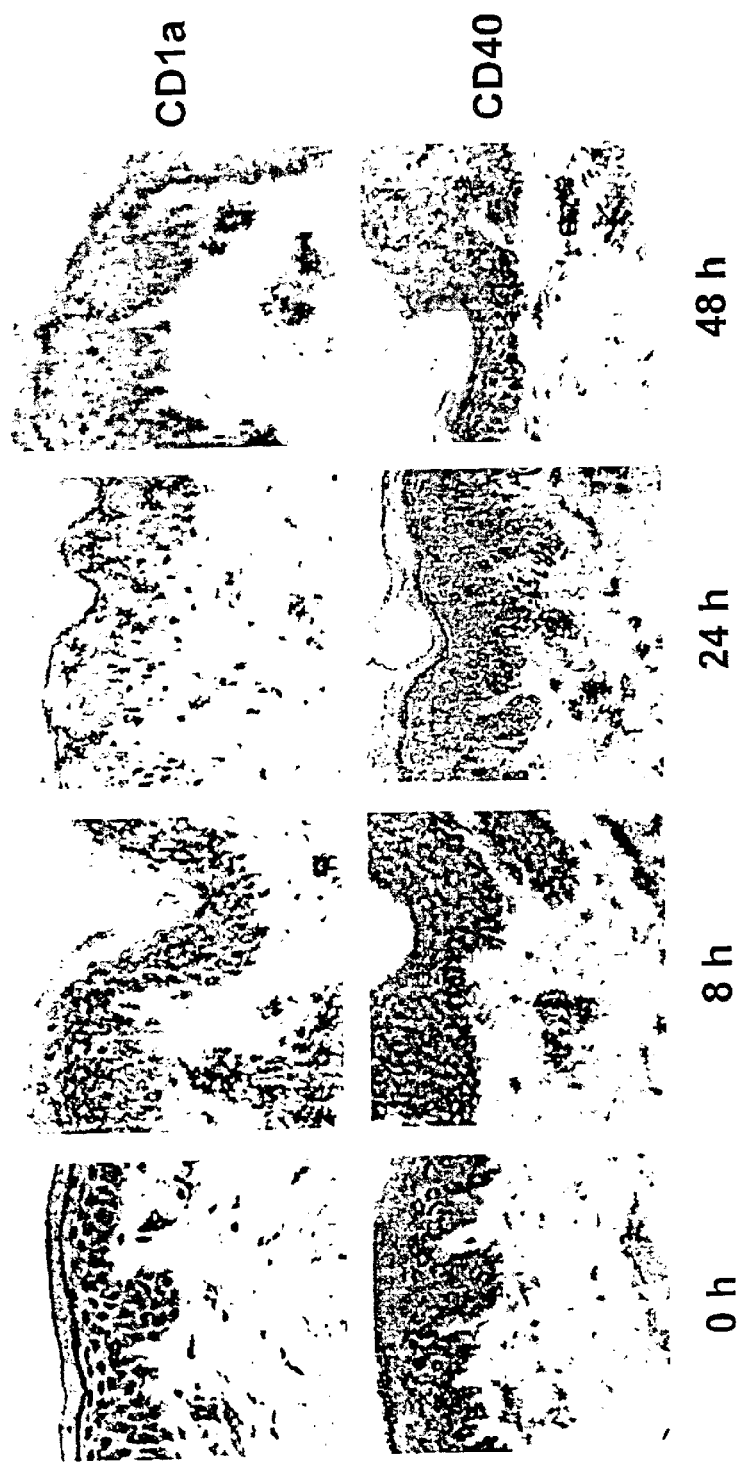
FIG. 18A shows the expression of CD1α and CD40 in epidermis and dermis of skin explants at 0, 8, 24 and 48 hours after i.d. injection of GM-CSF, 100× magnification.
Figure 18B:
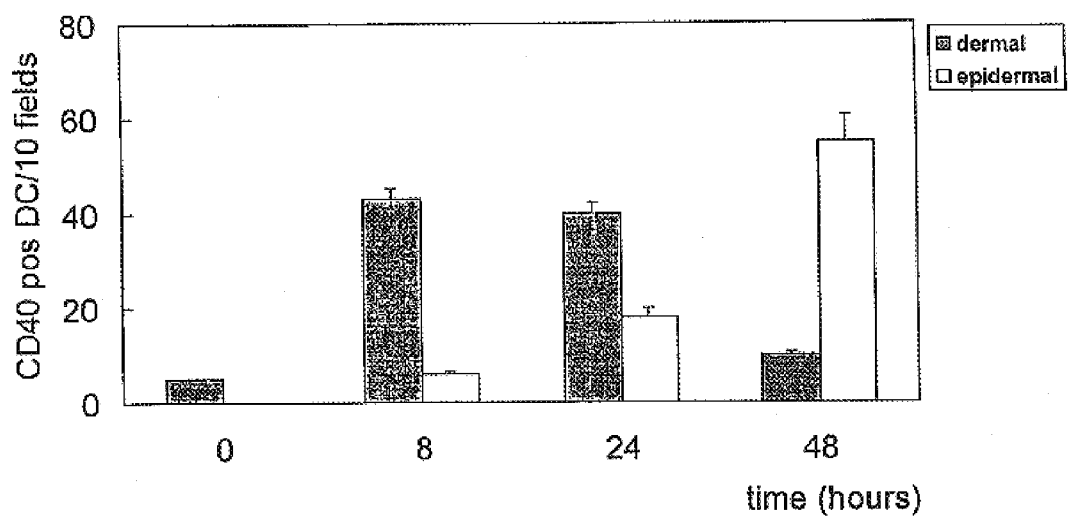
FIG. 18B shows the quantitation of CD40+ DC in the epidermis and dermis of skin explants at the indicated time points after GM-CSF injection.

The utility of the CD40-targeted adenoviral gene transfer for selective in situ gene transfer to dendritic cell after intradermal (i.d.) injection was examined in a human skin explant model. The usefulness of CD40-targeting depends critically on the relative expression levels of CD40 on the target dendritic cell and on other non-APC, such as keratinocytes, fibroblasts, and endothelial cells, which also have the ability to express CD40 under certain inflammatory conditions. As shown in FIG. 18A, in freshly explanted skin, dendritic cell are distributed throughout the dermis and epidermis, as visualized by CD1α and HLA-DR (not shown) staining and their typical morphologic dendritic appearance. However, only a very weak basal expression of CD40 was observed on cells with dendritic cell morphology. After i.d. injection of granulocyte-macrophage stimulating factor (GM-CSF), optimal activation of DC was observed at a dose of 100 ng GM-CSF. A marked increase in the expression levels of CD1α on dendritic cells both in the dermis and in the epidermis was observed 24 h after i.d. injection of 100 ng GM-CSF (FIG. 18A). In addition, an increased expression of HLA-DR (not shown) and CD40 (FIG. 18A) indicated maturation of the dendritic cells. This was also confirmed by the expression of the dendritic cell maturation marker CD83 (data not shown). Enumeration of CD40 expressing dendritic cells over time (FIG. 18B) indicates a marked increase after 8 hours. By 48 hours after injection the number of CD1α+ dendritic cells were decreasing, probably due to migration out of the skin (FIG. 18A). Weak and diffuse expression of CD40 in the basal layer of the epithelium and on endothelial cells was also observed 24 h after GM-CSF injection. However, this expression was much lower as compared, to the expression of CD40 on DC. In keeping with previous findings, the cutaneous dendritic cells did not express the primary Ad receptor CAR, but did express the integrin $α_vβ_5$, which acts as coreceptor and mediates Ad internalization (data not shown).

CD40-targeted Gene Transfer to Cutaneous DC in situ

Figure 19:
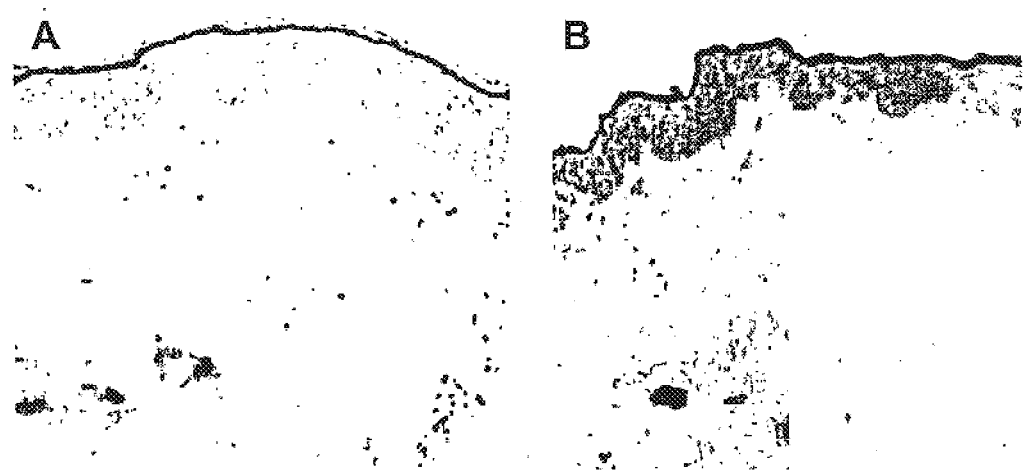
FIG. 19A shows the nuclear expression of β-Gal after i.d. injection of 100 ng GM-CSF and $10^8$ pfu Ad-LacZ.
FIG. 19B shows the nuclear expression of β-Gal after i.d. injection of 100 ng GM-CSF and $10^8$ pfu Ad-LacZ complexed to the CD40-targeting conjugate. (magnification 100×; insert 400×). $10^8$ pfu of Ad was added to 833 ng Fab-anti-CD40 and incubated at room temperature for 30 min before injection into the skin explants. For the enzymatic staining of cells transduced with the LacZ gene encoding for β-galactosidase, slides were incubated with β-gal staining solution (Boehringer Mannheim, Germany) for 12–72 hours at 37° C. after fixation with 2% formaldehyde and 0.2% glutaraldehyde in PBS for 15 minutes.
Figure 20:
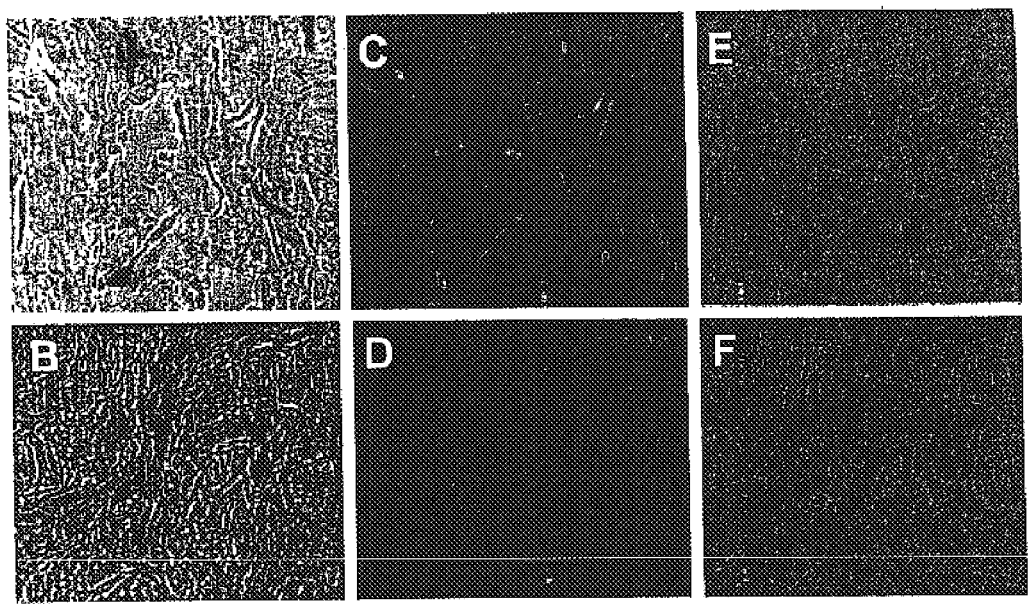
FIG. 20A shows the expression of β-Gal by dermal cells after i.d. injection of 100 ng GM-CSF and $10^8$ pfu Ad-LacZ (400×).
FIG. 20B shows the expression of β-Gal by dermal cells after i.d. injection of 100 ng GM-CSF and $10^8$ pfu Ad-LacZ complexed to the CD40 targeting conjugate (400×).
FIG. 20C shows the cells transduced by untargeted Ad-LacZ to be CD1α negative upon double staining with PE-labeled antibody.
FIG. 20D shows the cells transduced by CD40-targeted Ad-LacZ to be CD1α positive upon double staining with PE-labeled antibody.
FIG. 20E shows the overlays of β-Gal and CD1α expression for the untargeted conditions.
FIG. 20F shows the overlays of β-Gal and CD1α expression for the CD40-targeted conditions.
FIG. 20G shows the quantitation of the number of CD1α positive or CD1α negative β-Gal+ cells in the dermis of the Ad-injected skin explants (representative results from one out of three experiments are shown).
Figure 20G:
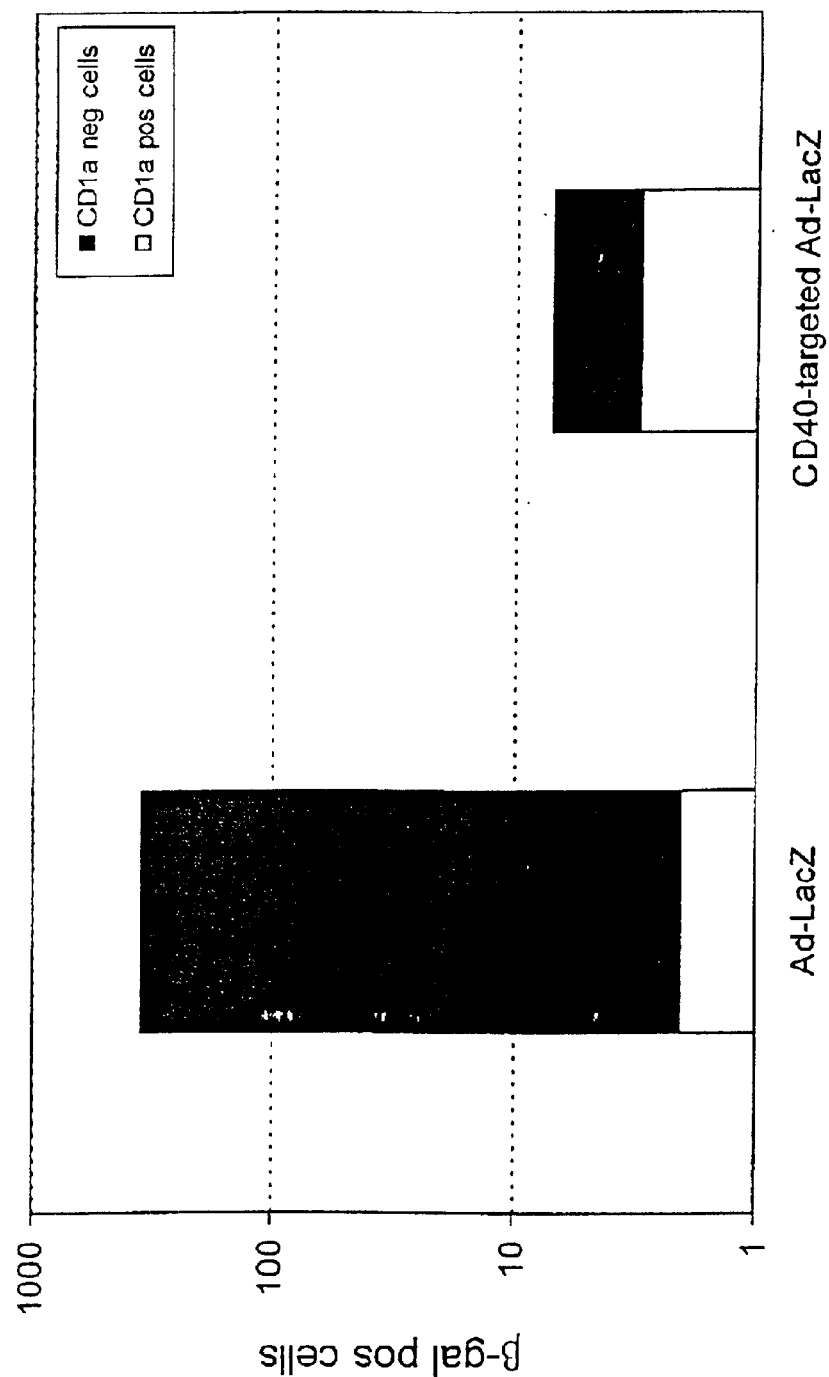

Skin explants were injected i.d. with 100 ng GM-CSF in combination with an unconjugated adenoviral vector encoding LacZ (Ad-LacZ) or with Ad-LacZ complexed to a chemically linked bispecific antibody conjugate directed to the fiber knob region of the Ad capsid and to CD40 (Fab-anti-CD40). After 48 h β-Galactosidase (β-Gal) activity was scored on sections. The optimal dose of Ad-LacZ was determined to be $10^8$ pfu per injection. Injection of Ad-LacZ resulted in the transduction of a high number of cells within the dermis, but not in the epidermis (FIG. 19A). Double staining with a PE-labeled antibody demonstrated a vast majority (more than 99%) of these cells to be CD1a negative (FIGS. 20A, C, E, G). In contrast, injection of Fab-anti-CD40-complexed Ad-LacZ resulted in a drastic reduction of the absolute number of transduced cells (FIG. 19B), but in a considerable increase in the proportion of CD1α+ transduced cells (more than 50%, FIGS. 20B, D, F, G), thus revealing a more selective targeting to DC.

In parallel, Ad-LacZ complexed to Fab-anti-EGFR (a bispecific antibody conjugate targeting Ad to the epidermal growth factor receptor) was also injected into skin explants. No β-Gal activity was ever detected using this conjugate (data not shown), indicating an effective blocking of the natural tropism of Ad and excluding the possibility of Ad uptake by binding of antibodies in the conjugate to Fc receptors on the surface of DC.

Migration of Transduced DC

Central to the capacity of DC to start an immune response in vivo is their ability to migrate from the vaccination site (i.e. dermis) to the draining lymph node (LN), where subsequent T cell activation occurs. Hence, the ability of DC transduced either by untargeted or CD40-targeted Ad vectors to migrate from the skin explants was examined. To obtain migrated DC, Ad-injected and Fab-anti-CD40-Ad-injected explants were placed directly in culture medium (12 explants per test condition). GM-CSF was injected i.d. simultaneously with the Ad vector, and explants injected with GM-CSF alone were included as controls. After 48 h the medium was collected, pooled per condition and from the migrated cells cytospins were made (±3000 cells per cytospot). The number of migrated cells varied per experiment from 1000 to 5000 per skin explant. Most cells had the typical morphologic DC appearance of large cells, with a lobulated nucleus and long veils. Immunohistochemical analysis revealed the majority of migrated cells (>70%) to be CD1α+ DC with a mature phenotype, showing high levels of HLA-DR, CD54, and CD86 expression and a heterogeneous expression of CD83. FIG. 21A shows the typical morphology of these cells on cytospin after HLA-DR staining. The mature phenotype of at least a subpopulation of these DC is further indicated by their adherence to HLA-DR negative lymphocytes co-migrating from the skin explants as previously described [Mclellan et al., 1998, J. Invest. Dermatology, 111:841].

Figure 21C:
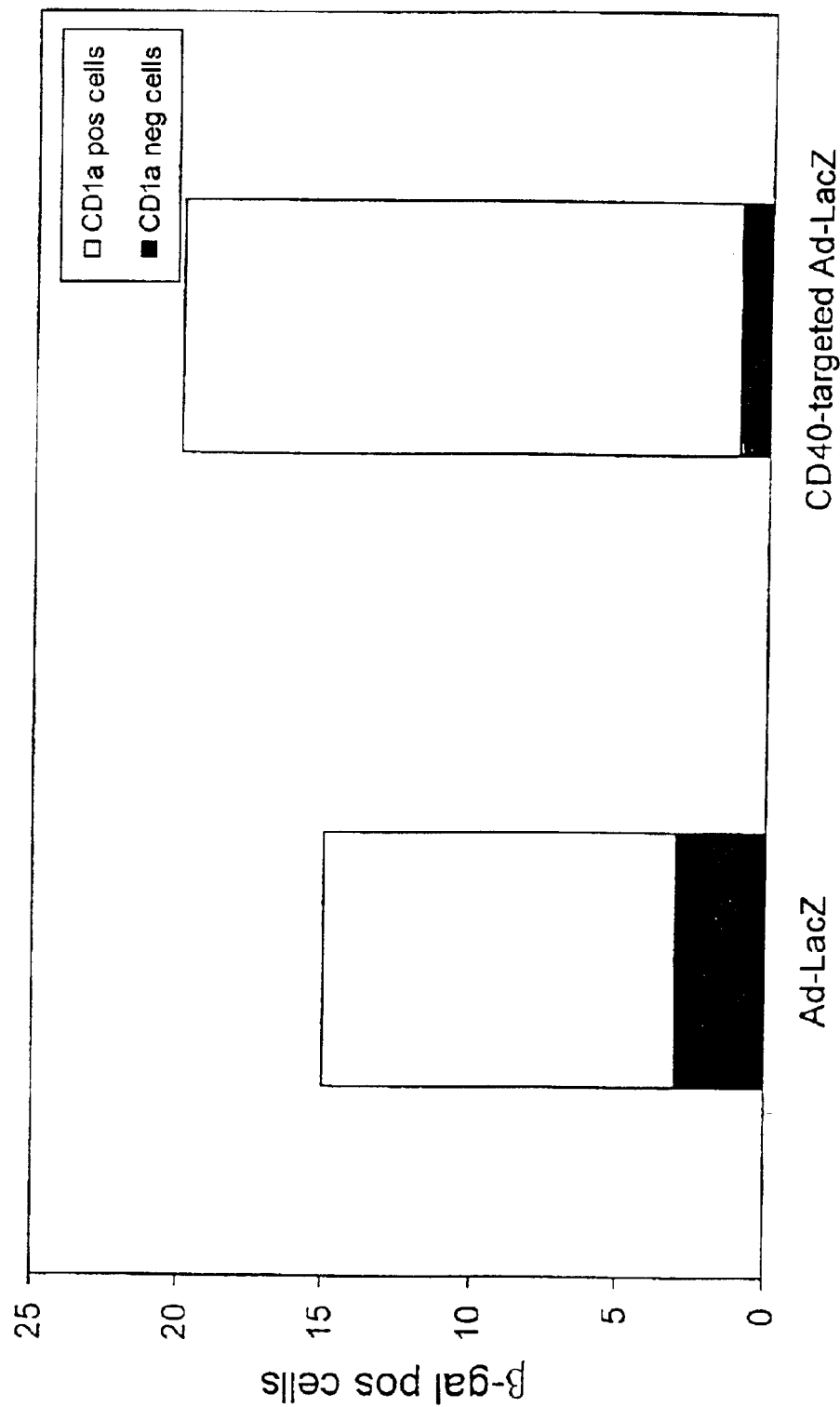
FIG. 21C shows the quantitation of β-Gal expressing (CD1α+/−) migrated cells 48 hours after injection of GM-CSF and Ad vectors (one representative experiment out of three is shown).

By CD1α-PE and β-Gal double staining, LacZ-transduced DC could be detected among the migrated DC on cytospins (FIG. 21B). No significant difference in the number of migrated β-Gal⁺ DC from explants injected with either CD40-targeted or untargeted Ad could be detected after counting of these CD1α⁺/β-Gal⁺ DC in ten high power (400×) magnification fields (FIG. 21C). The very small proportion of transduction cells precluded the reliable calculation of transduction efficiency, which will have to await more large-scale migration assays after injection of an Ad-vector encoding the Green Fluorescent Protein that would allow for a more sensitive and reliable quantitation of the transduced cell fraction and the simultaneous phenotypic characterization of both transduced and non-transduced DC by FACS analysis.

Previous studies in skin biopsies reported spontaneous migration of DC after 48 hours of culture [Larsen et al., 1990, J. Exp. Med.; Lukas et al., 1996, J. Invest. Dermatology, 106:1293]. The results shown above indicate that Ad-transduced DC retained this ability. Nor did the binding of the Fab-anti-CD40 conjugate impair migration. This is in keeping with previous murine studies which showed a similar or slightly enhanced number of ex vivo generated DC, injected into the dermis, to migrate to skin-draining LN after maturation by CD40L [Labeur et al., 1999, J. Immunol. 162:168].

In conclusion, i.d. CD40-targeted delivery of adenoviruses leads to a more selective in situ transduction of CD1α⁺ DC, without interfering with their migratory ability. In vivo targeting of antigen to dendritic cells provides an attractive immunotherapeutic alternative to the laborious ex vivo generation and antigen-loading of autologous dendritic cells followed by adoptive transfer. Combined with the observation of an increased in vitro T cell stimulatory ability of CD40-Ad transduced dendritic cells, these characteristics make this CD40-targeted Ad delivery system a promising new immunotherapeutic modality.

EXAMPLE 5

Ablation of Coxsackie-Adenovirus Receptor (CAR)-Dependent Adenovirus Tropism and Incorporation of Heterologous Ligands by Means of an Ad5 Fiber-T4 Fibritin Hybrid Since fiber knob is known to mediate the interaction of adenovirus with CAR, replacement of the fiber knob by a targeting molecule not only results in an adenovirus with new binding abilities but also causes complete ablation of its natural tropism. In order to modify the adenovirus fiber, however, it should be noted that adenovirus fiber possesses a quaternary configuration with strict structural limitations. The adenovirus fiber is synthesized as a monomer which undergoes trimerization in the cytoplasm before translocation to the nucleus, where viral particles are assembled [Hong and Engler, Virology, 1991. 185:758]. Trimeric fibers then associate with the pentameric penton base through their amino terminus. It is known that the fiber knob plays a key role in trimerization. Deletion of even small portions of the knob destabilizes the entire fiber and results in monomeric forms of the protein which can not associate with the penton base protein and incorporate into mature adenovirus virions [Hong and Engler, J Virol, 1996. 70:7071; Novelli and Boulanger, Virology, 1991. 185:365]. Thus, it is necessary to genetically modify the fiber without impairing its trimerization capability. For the purpose of this study, the entire knob domain is deleted and substituted with two distinct protein moieties each capable of performing one of the two functions of the fiber knob. Therefore, one of these protein structures, i.e., the trimerization domain, initiates and maintains the trimeric configuration of the protein while the other one, i.e., targeting domain, serves as a receptor-specific cell-binding ligand.

Recombinant fiber proteins lacking the knob domain were designed, which were capable of trimerizing and incorporating targeting ligands. In order to provide trimerization function for a knob-deleted fiber molecule, bacteriophage T4 fibritin protein was utilized, which forms the so-called whiskers of the T4 virion. Fibritin is a rod-like homotrimeric molecule containing a compact carboxy terminal trimerization motif. Deletion of amino-terminal portions of the fibritin molecule does not affect its trimerization [Miroshnikov et al., Protein Eng, 1998. 11:329; Efimov et al., J Mol Biol, 1994. 242:470]. It has also been shown that additions of heterologous protein sequences to the carboxy-terminus of the fibritin are compatible with fibritin trimerization [Miroshnikov et al., Protein Eng, 1998. 11:329]. Therefore, it would be possible to incorporate the Ad5 fiber tail domain in the fibritin amino-terminal region and a targeting ligand in the carboxy-terminus without affecting trimerization (FIG. 22).

Figure 23:
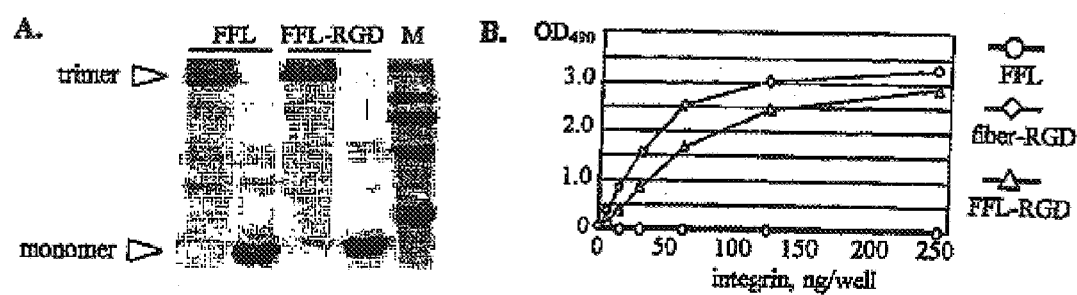
FIG. 23 shows evaluation of the fiber-fibritin chimeras expressed in E.coli.

A recombinant fiber gene was designed encoding a chimeric protein consisting of the tail and a portion of the shaft domain of Ad5 fiber fused to the carboxy-terminal portion of the T4 fibritin, followed by a short peptide linker. In addition, the 5' end of the gene was designed to encode a six histidine tag, for purification purposes. The recombinant gene was cloned in the *E.coli* expression plasmid pQE30. Induction of expression of the fiber-fibritin-linker protein chimera resulted in production of a protein of the expected molecular weight, as detected in the lysates of induced bacteria with both an anti-fiber tail monoclonal antibody (4D2) and an anti-fibritin polyclonal serum. Purification of the recombinant protein by Ni-NTA Sepharose (which binds the His tag) resulted in 95%. pure product suitable for subsequent analysis. Gel electrophoresis analysis of the purified product revealed that virtually all of the protein in a non-denatured sample is in trimeric form (FIG. 23A).

A targeting ligand was next introduced in the fiber-fibritin-linker chimera by cloning an RGD-4C sequence (RGD-4C peptide=CDCRGDCPC, SEQ ID No. 1) in the 3' end. This RGD motif binds specifically to αvβ3 and αvβ5 integrins [Plasqualini and Ruoslahti, Nat. Biotechnol., 1998. 15:542]. This fiber-fibritin-linker-RGD chimera was purified by chromatography and was also shown to be in a trimeric form (FIG. 23A). Accessibility of the RGD-4C peptide for binding to receptor molecules was assayed by ELISA utilizing purified integrin αvβ3 protein. An untargeted fiber-fibritin-linker protein was used as a negative control of binding while a fiber-RGD protein was used as a positive control. The results (FIG. 23B) indicate that the chimeric fiber-fibritin protein containing an RGD motif is able to bind specifically to αvβ3 integrins, unlike its untargeted counterpart.

Taken together, the data indicate that by means of an Ad5 fiber tail- T4 fibritin hybrid protein, 1) it is feasible to eliminate the Ad5 fiber knob while retaining the trimerization requirements and 2) it is possible to incorporate ligands to generate fiber-like proteins with new binding specificities.

EXAMPLE 6
Generation of Replication-Deficient Ad Vectors Containing Modified Fiber Proteins Since targeted viruses with modified fiber proteins as described above have CAR natural binding completely ablated, they should no longer be able to replicate in packaging cell lines like 293 that do not express the targeted receptors. An alternative way was designed to generate and produce modified vectors.

Figure 24:
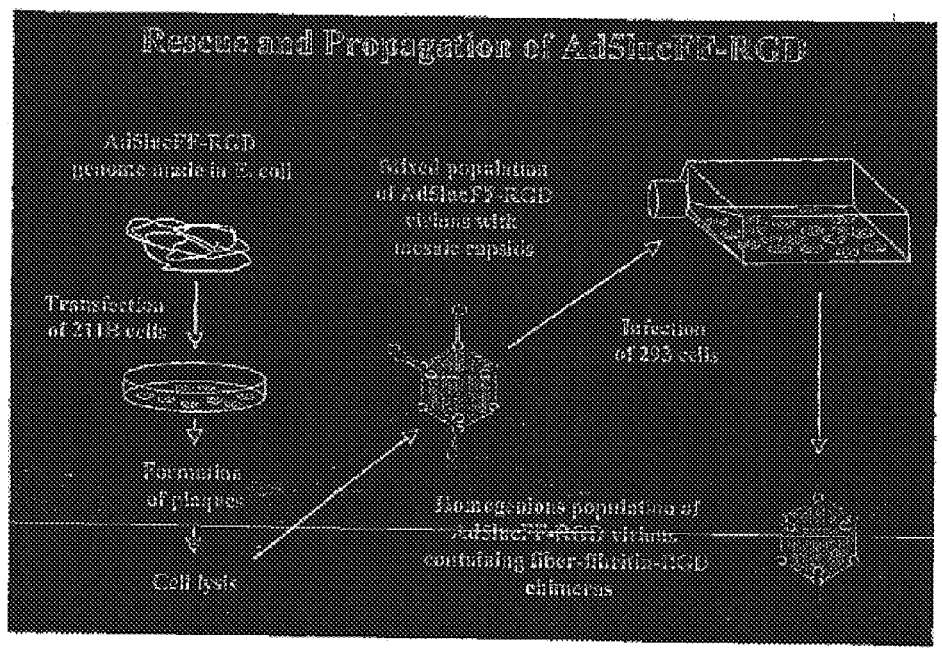
FIG. 24 shows rescue and propagation of fiber-modified Ad virions. In order to facilitate plaque formation by the fiber-modified Ad, 211B cells which constitutively express the wild type fiber are used for transfection with the recombinant Ad genome derived in E.coli. Rescued viruses are then propagated in 211B cells to provide enough viral material for large-scale infection of 293 cells, which results in a homogeneous population of virions containing the modified fibers.

A system was developed to generate and propagate Ad with genetically modified fibers based on the combination of two strategies: 1) homologous DNA recombination in E.coli to generate a recombinant adenovirus genome containing the transgene and the modified fiber; and 2) transfection of a 293-derived packaging cell line that expresses the wild type fiber protein constitutively (FIG. 24).

Figure 25:
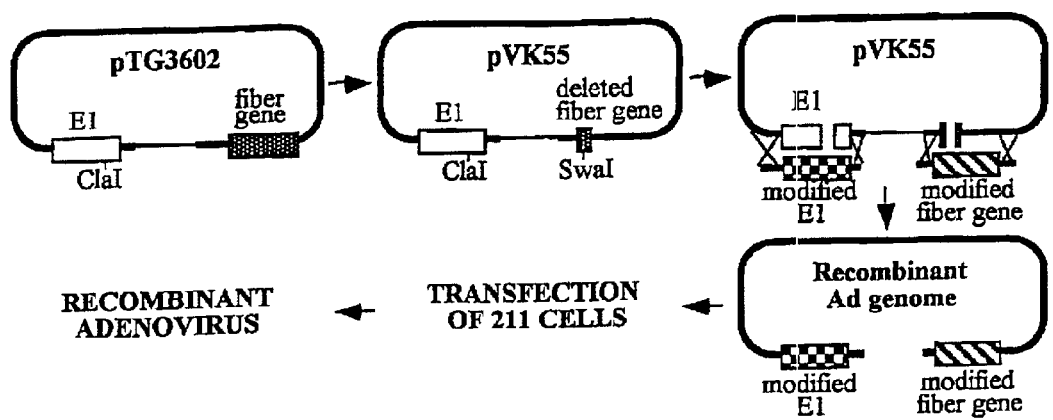
FIG. 25 shows schema of derivation of recombinant Ad employing pVK55. Unique restriction sites ClaI and SwaI within pVK55 are used to cleave the plasmid in order to selection of plasmids containing recombinant Ad genomes. Plasmid backbone is then excised by additional restriction enzyme digestion (not shown) and resultant DNA is used for transfection of 211 cells for rescuing the virus of interest. Sequences of the original and modified Cla I sites in pTG3602 and pVK55, respectively, are shown in paretheses.

The homologous recombination system in E.coli was originally developed by Chartier et al [J Virol, 1996. 70:4805]. Plasmid pTG3602 containing a full size Ad5 genome was modified to delete most of the fiber open reading frame and incorporate a unique restriction site, SwaI, in place of the deleted sequence. In order to introduce expression cassettes in the E1 region, the flanking nucleotides of the unique restriction site, ClaI, was mutated thus rendering the site methylation-resistant as opposed to the wild type sequence. This gave rise to plasmid pVK55 (FIG. 25). Co-transformation of E.coli with ClaI/SwaI cleaved pVK55 and DNA fragments containing the modified fiber genes or substituted E1 regions allows the generation of recombinant Ad genomes. Because plasmid pVK55 has been linearized prior to co-transformation, only recircularized recombinant genomes will give rise to transformants.

This system has been successfully used to generate a series of recombinant adenoviral genomes containing various fiber genes as well as different payloads in place of E1. Because adenovirus containing modified fibers will not be able to propagate in classical packaging cell lines like 293, 911 or PERC6, 211B cell line (kindly provided by Dr. von Seggern and Dr. G. Nemerow, The Scripps Research Institute, La Jolla, Calif.) was employed that constitutively expresses the Ad5 fiber protein along with the E1 proteins. Transfection of 211B with the recombinant Ad genome generates virions with heterogeneous capsids containing both wild type and modified fibers. A final round of infection in 293 cells generates virions with homogeneous capsids containing only the modified fiber. In this regard, the fiber-deleted genome contained in plasmid pVK55 was packaged in 211B cells.

EXAMPLE 7
Construction of a Genetically Modified Ad Vector with Targeted Binding to CD40 and Analysis of Its Specificity and Efficiency of Transduction in vitro In the present study, the natural adenovirus binding was abolished and targeting to CD40 via genetic modification of the adenovirus fiber was achieved. The feasibility of this part is supported by the previous experience in adenoviral capsid modification [Krasnykh et al., J Virol, 1996. 70:6839; Krasnykh et al., J Virol, 1998. 72:1844; Dmitriev et al., J Virol, 1998. 72:9706] and preliminary data as shown in Examples 5 and 6. Furthermore, the generation of a fiberless adenovirus by complete deletion of the L5 structural gene has been recently reported [Legrand et al., J Virol, 1999. 73:907; Von Seggern et al., J Virol, 1999. 73:1601]. These results demonstrate that deletion and possibly substitution of Ad fiber does not abrogate Ad packaging. As fiber knob is both required for trimerization of fiber as well as interaction of Ad with its natural CAR receptor, the T4 fibritin molecule was used as a trimerization domain and the CD40 ligand (CD40L) molecule as the targeting domain to DCs. Interestingly, CD40L has also been shown to function in a trimeric form. This particular characteristic of the CD40L will allow the study of whether it is possible to simply replace the fiber knob by the CD40L molecule while keeping the fiber shaft and tail. In this case, CD40L serves both as trimerization and ligand domains.

To proof this concept, the human CD40L molecule is used. The use of the human version will simplify the virus characterization since human cell lines expressing its cognate receptorCD40 have been characterized and are available as well as the CD40/CD40L cDNAs. Despite the degree of sequence identity between human and mouse CD40L (78%) [Spriggs et al., J Exp Med, 1992. 176:1543], it is known that human CD40L is orders of magnitude less active in mouse cells than its murine counterpart. Therefore, in order to perform preclinical studies in mouse models, a murine CD40L-modified adenovirus version is generated. The development of this new targeted Ad allows the study of the efficacy of dendritic cell transduction in an in vivo schema.

Construction of a Shuttle Plasmid Vector and Generation of an Adenoviral Vector Containing a CD40L-modified Fiber Because of the structural and functional. similarities between the adenovirus 5 fiber knob and the globular domain of the human CD40L, the fiber knob is replaced with the globular domain of CD40L. To this end, two different strategies are implemented. First, a fiber chimera composed by an adenovirus fiber tail plus the bacteriophage fibritin is generated in place of the natural fiber shaft followed by the CD40L globular domain. In the second strategy, the adenovirus fiber tail plus shaft is utilized to replace only the fiber knob with the globular domain of CD40L.

To generate the two CD40-modified fiber versions, the cDNA encoding human CD40L (obtained from ATCC) is utilized. Both chimeric constructs are extensively sequenced in order to assure absence of sequence errors. The DNA fragments encoding these two chimeric fibers are cloned in the pQE30 E.coli expression vector. The recombinant proteins produced are analyzed in an SDS-PAGE gel in both denaturing and non-denaturing conditions in order to ascertain the trimerization ability of the chimeric fibers. After assessing trimerization, the coding sequence for the chimeric fibers are each cloned in a shuttle vector for homologous recombination in E.coli. Further modification of the recombinant genomes can be achieved by inserting expression cassettes for reporter or tumor antigens in the E1 region deletion point. Generation of viral particles will require transfection of the recombinant genome in a suitable cell line that can support replication, production, and infection of the fiber-modified virus. In this regard, the expression of CD40 protein will be analyzed in the current packaging cell lines available, 293 and 911 cells, which is a requisite for the propagation of a CD40-targeted virus. In the absence of CD40 expression in these cell lines, a CD40-expressing 293 cell line will be generated for ease of vector large-scale preparation. For this purpose, the cDNA encoding human CD40 are provided by Dr. Stamenkovic (Department of Genetics, Harvard Medical School) and cloned in a mammalian expression vector like pcDNA-3 and transfected in 293 cells or another human E1-containing cell line. Neo-resistant clones will be analyzed for CD40 expression by Northern blot and immunoblot with specific antibodies. A positive clone with adequate levels of CD40 expression will be used as a packaging cell line for CD40-targeted adenovirus. To generate virions, the recombinant genomes corresponding to E1-substituted adenovirus containing a chimeric fiber are transfected in the CD40-packaging cell line. Alternatively, 211B cells (a 293-derived cell line expressing wild type fiber) can be used to generate these viruses because viruses produced in these cells will contain both wild type and chimeric fibers. In order to produce homogenous capsids, the last round of infection should be done in 293 cells. Large-scale preparation of CD40-targeted Ad will be purified by CsCl-banding by a standard protocol.

Characterization of the CD40L-modified Virus

After large-scale propagation and purification, virus particle number are quantified by optical density reading at 260 ($OD_{260}$). Plaque-forming units (pfu) will be estimated by plaque assay in the specific packaging cell line. The presence of CD40L in the virus capsid will be analyzed by western blot with specific antibodies to CD40L. To rule out the presence of wild type fiber, a monoclonal antibody recognizing the fiber tail will be used as a control. Structural analysis of the virions are performed by electronic microscopy. The appearance of the modified capsids are compared to non-modified capsids.

To demonstrate that the CD40-targeted Ad infects through a new CAR-independent pathway, inhibition assays is performed in the presence of increasing concentrations of soluble knob or soluble CD40L. The infectivity is measured as the percentage of transduced cells for a given M.O.I. These experiments will be done infecting cells with a serial dilution of the CD40-targeted vector carrying a GFP reporter gene and counting the number of transduced cells 24 hours after infection. It is expected that the presence of knob will not inhibit the infectivity of the modified virus in comparison to the unmodified Ad. Furthermore, the magnitude and specificity of the CD40L-modified Ad infectivity will be analyzed in different cell lines with known levels of CD40 and CAR expression. CD40-expressing cell lines have been described previously [Stamenkovic et al., Embo J, 1989. 8:1403] and include IM-9, CESS (B-lymphoblastoid), Raji (Burkitt lymphoma), HepG2 (colon carcinoma), and HS294T (melanoma). All of these cell lines can be obtained from ATCC. Cell lines with different levels of CD40 expression will be used to assess whether any direct correlation exists between CD40 expression and CD40-targeted Ad infectivity. It is expected to observe higher infectivity of the CD40-targeted Ad in cell lines with higher CD40 levels irrespective of the CAR levels. From the relative infectivity of the CD40-targeted Ad and the unmodified Ad in cell lines with high levels of both CD40 and CAR receptors, the efficacy of these infection pathways will be inferred.

At the end of this primary characterization with cell lines, the infectivity of the CD40-targeted Ad will be analyzed in DCs. Human DCs cultured ex vivo will be infected at different M.O.I. of the targeted and control Ad. As in the case of the immunologically CD40-targeted Ad, it is expected that a lower MOI of the targeted vector will yield the same transduction efficiency as compared to higher MOIs of the untargeted Ad.

CD40-targeted genetically modified Ad is used to deliver a specific tumor antigen into DCs and its vaccination potency is determined. To this end, preclinical studies are performed in an animal tumor model such as the above mentioned HPV E7-based model. A targeted Ad with the murine CD40L sequence is constructed. Murine CD40L has been cloned and it is available through ATCC. Similar procedures are followed for construction and generation as presented for human CD40-targeted Ad. The binding of murine CD40L to human CD40 has been reported to be of similar magnitude as for the human ligand [Spriggs et al., J Exp Med, 1992. 176:1543]. Therefore, human cell lines expressing human CD40 are used to propagate the murine CD40L-modified virus. In case this procedure would result inefficient, a cell line containing the homospecific CD40 are generated. For this purpose, murine CD40 cDNA are PCR amplified from an appropriate murine cDNA library, cloned in an expression vector and transfected in an Ad packaging cell line for selection of stable CD40L-expressing clones. Altogether, these experiments will demonstrate that it is feasible to replace the adenovirus fiber and to abrogate natural tropism while redirecting the binding to CD40.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A gene delivery system for CD40⁺ immune cells, comprising:
   (a) a recombinant adenovirus; and
   (b) a component recognizing CD40 antigen comprising a first antibody, or antigen-binding fragment thereof, that binds to a fiber-knob protein of said adenovirus, wherein said first antibody or antigen-binding fragment thereof is conjugated to a second antibody, or antigen-binding fragment thereof, that binds to CD40 antigen.

2. The gene delivery system of claim 1, wherein said first antibody and second antibody are genetically fused together.

3. The gene delivery system of claim 1, wherein said second antibody that binds to CD40 antigen is secreted from hybridoma selected from the group consisting of G28.5 (ATCC #9110-HB) and FGK45.

4. The gene delivery system of claim 1, wherein said gene delivery system mediates an effect selected from the group consisting of transduction of said CD40⁺ immune cells,, immunomodulation of said CD40⁺ immune cells, and maturation of said CD40⁺ immune cells.

5. The gene delivery system of claim 1, wherein said system further comprises a therapeutic gene.

6. The gene delivery system of claim 5, wherein said therapeutic gene is selected from the group consisting of a gene encoding a tumor antigen, a gene encoding an antigen for an infectious agent, a gene encoding an autoimmune antigen, an immunomodulatory gene and a gene encoding a cytotoxic agent.

7. The gene delivery system of claim 6, wherein said tumor antigen is human papillomavirus type 16 E7 antigen.

8. The gene delivery system of claim 1, wherein said CD40⁺ immune cells are selected from the group consisting of dendritic cells and B cells.

9. The gene delivery system of claim 8, wherein said dendritic cells are selected from the group consisting of monocyte-derived dendritic cells, bone marrow-derived dendritic cells and cutaneous dendritic cells.

10. A method for genetically manipulating CD40⁺ immune cells, comprising the step of:
    administering the gene delivery system of claim 1 to said CD40⁺ immune cells, wherein said gene delivery system mediates gene transduction and causes maturation of said CD40⁺ immune cells.

11. The method of claim 10, wherein said CD40⁺ immune cells are obtained from individual who has a disease selected from the group consisting of cancer, an infectious disease, allotransplant rejection, xenotransplant rejection and an autoimmune disease.

12. The method of claim 10, wherein said administration of the gene delivery system is selected from the group consisting of systemic administration, intradermal administration and ex vivo administration.

13. A method for genetically manipulating CD40⁺ immune cells, comprising the step of:
    administering the gene delivery system of claim 5 to said CD40⁺ immune cells, wherein said gene delivery system mediates gene transduction and causes maturation of said CD40⁺ immune cells.

14. The method of claim 13, wherein said CD40⁺ immune cells are obtained from individual who has a disease selected from the group consisting of cancer, an infectious disease, allotransplant rejection, xenotransplant rejection and an autoimmune disease.

15. The method of claim 13, wherein said administration of the gene delivery system is selected from the group consisting of systemic administration, intradermal administration and ex vivo administration.

16. A method for enhancing the vaccination potential of dendritic cells, comprising the step of:
    administering the gene delivery system of claim 1 to said dendritic cells, wherein said gene delivery system mediates gene transduction and increases the vaccination potential of said dendritic cells.

17. The method of claim 16, wherein said dendritic cells are obtained from individual who has a disease selected from the group consisting of cancer, an infectious disease, allotransplant rejection, xenotransplant rejection and an autoimmune disease.

18. The method of claim 16, wherein said administration of the gene delivery system is selected from the group consisting of systemic administration, intradermal administration and ex vivo administration.

19. A method for enhancing the vaccination potential of dendritic cells, comprising the step of:
    administering the gene delivery system of claim 5 to said dendritic cells, wherein said gene delivery system mediates gene transduction and increases the vaccination potential of said dendritic cells.

20. The method of claim 19, wherein said dendritic cells are obtained from individual who has a disease selected from the group consisting of cancer, an infectious disease, allotransplant rejection, xenotransplant rejection and an autoimmune disease.

21. The method of claim 19, wherein said administration of the gene delivery system is selected from the group consisting of systemic administration, intradermal administration and ex vivo administration.

22. The gene delivery system of claim 1, wherein said system is a recombinant adenoviral vector.

23. The gene delivery system of claim 5, wherein said system is a recombinant adenoviral vector.

24. The method of claim 10, wherein said gene delivery system is a recombinant adenoviral vector.

25. The method of claim 13, wherein said gene delivery system is a recombinant adenoviral vector.

26. The method of claim 16, wherein said gene delivery system is a recombinant adenoviral vector.

27. The method of claim 19, wherein said gene delivery system is a recombinant adenoviral vector.

28. A recombinant adenoviral vector, comprising:
    a genetically modified adenovirus having a fiber protein comprising CD40 ligand, wherein the fiber shaft of said fiber protein is replaced by bacteriophage T4 fibritin protein and said CD40 ligand targets said vector to CD40.

29. A gene delivery system for CD40$^+$ immune cells, comprising:

the recombinant adenoviral vector of claim 28.

30. The gene delivery system of claim 29, wherein said gene delivery system mediates an effect selected from the group consisting of transduction of said CD40$^+$ immune cells, immunomodulation of said CD40$^+$ immune cells, and maturation of said CD40$^+$ immune cells.

31. The gene delivery system of claim 29, wherein said CD40$^+$ immune cells are selected from the group consisting of dendritic cells and B cells.

32. The gene delivery of claim 31, wherein said dendritic cells are selected from the group consisting of monocyte-derived dendritic cells, bone marrow-derived dendritic cells and cutaneous dendritic cells.

33. The gene delivery system of claim 29, further comprising:

a tumor antigen expression cassette, wherein said cassette is inserted into the E1 region of the modified adenovirus.

34. The gene delivery system of claim 33, wherein said tumor antigen is human papillomavirus type 16 E7 antigen.

35. A method for enhancing the vaccination potential of dendritic cells, comprising the step of:

administering the gene delivery system of claim 29 to said dendritic cells, wherein said gene delivery system mediates gene transduction and increases the vaccination potential of said dendritic cells.

36. The method of claim 35, wherein said dendritic cells are obtained from individual who has a disease selected from the group consisting of cancer, an infectious disease, allotransplant rejection, xenotransplant rejection and an autoimmune disease.

37. The method of claim 35, wherein said administration of the gene delivery system is selected from the group consisting of systemic administration, intradermal administration and ex vivo administration.

38. A method for enhancing the vaccination potential of dendritic cells, comprising the step of:

administering the gene delivery system of claim 33 to said dendritic cells, wherein said gene delivery system mediates gene transduction and increases the vaccination potential of said dendritic cells.

39. The method of claim 38, wherein said dendritic cells are obtained from individual who has a disease selected from the group consisting of cancer, an infectious disease, allotransplant rejection, xenotransplant rejection and an autoimmune disease.

40. The method of claim 38, wherein said administration of the gene delivery system is selected from the group consisting of systemic administration, intradermal administration and ex vivo administration.

41. The recombinant adenoviral vector of claim 28, wherein said CD40 ligand comprises the globular domain of CD40 ligand.

42. A gene delivery system for CD40$^+$ immune cells, comprising:

the recombinant adenoviral vector of claim 41.

43. The gene delivery system of claim 42, wherein said gene delivery system mediates an effect selected from the group consisting of transduction of said CD40$^+$ immune cells, immunomodulation of said CD40$^+$ immune cells, and maturation of said CD40$^+$ immune cells.

44. The gene delivery system of claim 42, wherein said CD40$^+$ immune cells are selected from the group consisting of dendritic cells and B cells.

45. The gene delivery of claim 44, wherein said dendritic cells are selected from the group consisting of monocyte-derived dendritic cells, bone marrow-derived dendritic cells and cutaneous dendritic cells.

46. The gene delivery system of claim 42, further comprising:

a tumor antigen expression cassette, wherein said cassette is inserted into the E1 region of the modified adenovirus.

47. The gene delivery system of claim 46, wherein said tumor antigen is human papillomavirus type 16 E7 antigen.

48. A method for enhancing the vaccination potential of dendritic cells, comprising the step of:

administering the gene delivery system of claim 42 to said dendritic cells, wherein said gene delivery system mediates gene transduction and increases the vaccination potential of said dendritic cells.

49. The method of claim 48, wherein said dendritic cells are obtained from individual who has a disease selected from the group consisting of cancer, an infectious disease, allotransplant rejection, xenotransplant rejection and an autoimmune disease.

50. A method for enhancing the vaccination potential of dendritic cells, comprising the step of:

administering the gene delivery system of claim 46 to said dendritic cells, wherein said gene delivery system mediates gene transduction and increases the vaccination potential of said dendritic cells.

51. The method of claim 50, wherein said dendritic cells are obtained from individual who has a disease selected from the group consisting of cancer, an infectious disease, allotransplant rejection, xenotransplant rejection and an autoimmune disease.

* * * * *

UNITED STATES PATENT AND TRADEMARK OFFICE
CERTIFICATE OF CORRECTION

PATENT NO. : 6,841,540 B1  
APPLICATION NO. : 09/591737  
DATED : January 11, 2005  
INVENTOR(S) : Curiel et al.

Page 1 of 1

It is certified that error appears in the above-identified patent and that said Letters Patent is hereby corrected as shown below:

In the Specification

Column 1, Line 14 Please replace the entire paragraph under the section entitled FEDERAL FUNDING LEGEND with the following paragraph:
This invention was made with government support under grant number CA074242 awarded by the National Institutes of Health. The government has certain rights in the invention.

Signed and Sealed this
Fourteenth Day of April, 2020

Andrei Iancu
*Director of the United States Patent and Trademark Office*

SEQUENCE LISTING

<160> NUMBER OF SEQ ID NOS: 1

<210> SEQ ID NO 1
<211> LENGTH: 9
<212> TYPE: PRT
<213> ORGANISM: Unknown
<220> FEATURE:
<221> NAME/KEY: DOMAIN
<222> LOCATION:
<223> OTHER INFORMATION: RGD motif that binds specifically to _v_3 and
      _v_5 integrins

```
<400> SEQUENCE: 1

Cys Asp Cys Arg Gly Asp Cys Phe Cys
                  5
```